US010215874B2

(12) United States Patent
Smoot

(10) Patent No.: US 10,215,874 B2
(45) Date of Patent: Feb. 26, 2019

(54) CAPACITIVE BASED SYSTEM TO DETECT OBJECTS BEHIND AN OBSCURING SURFACE

(71) Applicant: Lanny Starkes Smoot, Thousand Oaks, CA (US)

(72) Inventor: Lanny Starkes Smoot, Thousand Oaks, CA (US)

( * ) Notice: Subject to any disclaimer, the term of this patent is extended or adjusted under 35 U.S.C. 154(b) by 0 days.

(21) Appl. No.: 15/904,313

(22) Filed: Feb. 24, 2018

(65) Prior Publication Data

US 2018/0252832 A1 Sep. 6, 2018

Related U.S. Application Data

(63) Continuation of application No. 15/353,696, filed on Nov. 16, 2016, now Pat. No. 9,903,975.

(51) Int. Cl.
| | | |
|---|---|---|
| *G01R 27/26* | (2006.01) | |
| *G01V 3/02* | (2006.01) | |
| *G01V 3/38* | (2006.01) | |
| *G01N 27/22* | (2006.01) | |
| *G01D 5/24* | (2006.01) | |
| *G01R 27/00* | (2006.01) | |
| *G06F 3/044* | (2006.01) | |
| *G01N 22/00* | (2006.01) | |

(52) U.S. Cl.
CPC ............ *G01V 3/02* (2013.01); *G01D 5/2405* (2013.01); *G01N 27/22* (2013.01); *G01R 27/00* (2013.01); *G01R 27/26* (2013.01); *G01R 27/2605* (2013.01); *G01V 3/38* (2013.01); *G01N 22/00* (2013.01); *G06F 3/044* (2013.01)

(58) Field of Classification Search
CPC .... G01R 27/2605; G01R 27/26; G01R 27/00; G01D 5/2405; G06F 3/044; G01N 22/00
USPC .......... 324/76.11–76.83, 600, 635, 644, 649, 324/658, 662, 663, 671, 716
See application file for complete search history.

(56) References Cited

U.S. PATENT DOCUMENTS

| | | |
|---|---|---|
| 4,099,118 A | 7/1978 | Franklin et al. |
| 4,853,617 A | 8/1989 | Douglas et al. |
| 4,992,741 A | 2/1991 | Douglas et al. |
| 5,485,092 A | 1/1996 | Fortin |
| 5,617,031 A | 4/1997 | Tuttle |
| 5,774,091 A | 6/1998 | McEwan |
| 6,198,271 B1 | 3/2001 | Heger et al. |
| 6,249,113 B1 | 6/2001 | Krantz et al. |
| 6,894,510 B2 | 5/2005 | Schmidt et al. |

(Continued)

*Primary Examiner* — Jermele M Hollington
*Assistant Examiner* — Raul Rios Russo
(74) *Attorney, Agent, or Firm* — Thomas A. Runk; Brooks Kushman P.C.

(57) ABSTRACT

A capacitive detection and display device and method is used to simultaneously detect and display an image of an object hidden behind an obscuring surface. An electrode applies an electric field to a chamber having a visual display material which is located between the electrode and the obscuring surface. A sensitivity enhancement device is located within the electric field between the chamber and the obscuring surface to increase the sensitivity of the detection and display device and increase its depth of penetration through the obscuring surface. In one embodiment, the sensitivity device comprises an array of sensitivity electrodes formed on a nonconductive substrate. The shape of a hidden object is visually displayed by the visual display material.

20 Claims, 13 Drawing Sheets

(56) References Cited

U.S. PATENT DOCUMENTS

| | | |
|---|---|---|
| 7,053,599 B2 | 5/2006 | Clauss et al. |
| 7,116,091 B2 | 10/2006 | Miller |
| 7,148,703 B2 | 12/2006 | Miller |
| 7,982,450 B2 * | 7/2011 | Smoot ............... G01V 3/088 |
| | | 324/519 |
| 3,026,711 A1 | 9/2011 | Krapf et al. |
| 8,638,086 B2 * | 1/2014 | Smoot ............... G01V 3/088 |
| | | 324/519 |
| 2007/0200547 A1 | 8/2007 | Chen |
| 2007/0210785 A1 | 9/2007 | Sanoner et al. |
| 2007/0273671 A1 * | 11/2007 | Zadesky ............ G06F 3/0338 |
| | | 345/173 |
| 2009/0230945 A1 | 9/2009 | Smoot |
| 2011/0254532 A1 | 10/2011 | Smoot |

* cited by examiner

CAPACITIVE BASED SYSTEM TO DETECT OBJECTS BEHIND AN OBSCURING SURFACE

This application is a continuation of U.S. application Ser. No. 15/353,696, filed Nov. 16, 2016, now U.S. Pat. No. 9,903,975, which applicant incorporates by reference.

BACKGROUND

The invention relates generally to the detection of objects located behind an obscuring surface, and more particularly, to a device and method that measures capacitance and based on the capacitance measurements, simultaneously detects and displays images of obscured objects.

Often in the fields of building construction, renovation, and repair, as well as for other purposes, it would be desirable to be able to view an image of objects located behind an obscuring surface, such as a wall. Generating an "X-Ray" type of a view of walls, floors, ceilings, and other obscuring surfaces to find the exact locations of any structural or facilities members hidden behind them would be a significant benefit. In many cases for safety purposes, it is essential to locate any pipes or wires before any penetration of an obscuring surface occurs. In other cases, there is a need to find the exact location of a stud or other bracing member behind the obscuring wall surface for use as a strong support for mounting a heavy object to the wall, such as a mirror. The mounting screw or screws of the object to be hung must penetrate not only the wallboard, but also must extend into the stud since wallboard by itself is typically not strong enough to hold up heavy objects.

One option to determine what exists behind an obscuring wall is to remove the obscuring wall or a part of it. This can be expensive and time consuming. Carpenters for instance, would vastly benefit from the ability to plan improvements by viewing what is behind an obscuring wall without the need for opening that wall. Such wall openings cause an even greater amount of work due to the required repair, closing, and patching of those walls. Electricians and plumbers would also benefit from the ability to determine the exact locations of various obstructions and clear areas behind obscuring wall surfaces so that they could more easily plan their wire or pipe runs. Being able to determine the existence of pipes, wires, conduits, studs, bracing members, and other features would make projects easier, more efficient, and in many cases, less expensive.

Home inspectors would like to be able to determine whether various contractors and homeowners have done their work according to applicable construction codes and whether the materials and fabrication techniques are according to applicable requirements. In most cases, construction inspections are required before an obscuring surface is erected. However, cases have arisen, due to timing or other events beyond the control of those involved, where an obscuring surface is put in place before the required inspection could be performed. In such a case, verifying that proper construction techniques were used may require removal of the wall or other obscuring surface, or at least opening access ports through the wall to allow visual inspections. This leads to the additional time and expense to close the (often multiple) access ports of the wall. Because existing devices and methods do not adequately permit an inspector to check construction materials and techniques that are hidden from view behind an obscuring wall, removal of the wall is the only option in some cases. However, if a device and method were provided that would give the inspector a clearer view of the hidden object or construction techniques, such a device and method may enable an inspector to approve the completed construction without requiring that the wall be removed.

Being able to obtain a display of what is located behind a wall, floor, or ceiling surface is desirable for various purposes, such as locating cavities in floor surfaces, joists, and other areas, determining where fasteners should go when assembling any type of non-conductive structures, locating studs behind plastic, or glass walls, and locating live or non-live wires. Other situations would also benefit from a detector or scanner that can provide an image of the structure or features behind an obscuring surface. For example, it is desirable to be able to scan for hidden wall cavities in buildings, scan for hidden compartments in airplane internal cabin structures, analyze non-ferrous boat hulls to find hidden contraband cavities and/or metal substructures, locate hidden items in suitcases, and locate contraband at schools and in other places.

Various technologies have been proposed to avoid having to open an obscuring wall to find objects located behind that wall. These range from a simple metal detector comprising a pivoting magnet, to more complex metal detectors (see U.S. Pat. No. 4,853,617), to capacitive sensor systems, to a short-range radar system (see U.S. Pat. No. 5,774,091). A simple "stud finder" has been available for many years that is often used in an attempt to find the vertical support studs of a wall. Such stud finders detect ferrous metals using a compass-like pivoting magnet. The magnet was often pivoted at its middle and had a rest position that would be parallel to an obscuring surface against which the housing of the detector was applied. A portion of the case in which the pivoting magnet was mounted was clear so that pivoting movement of the magnet could be seen. This stud finder was much more effective in commercial buildings were metal studs are used. In the typical home setting, the magnetic stud finder would only work with wooden studs by locating the metal nails used to mount the wallboard or wooden lath, or a ferrous nail used to attach a stud to the bottom plate of the wall. When the detector was moved along the wallboard, the magnet would pivot and point to a ferrous material in the wall. However this detector does not locate a wooden stud per se, it only locates a ferrous nail that may or may not be in the stud. It also does not provide a clear display of the nail it locates. The only display is that the magnet points in the direction of the nail. As the detector is moved across the wallboard that is obscuring sight of the nail, the magnet will continue to angle itself towards the nail, until its sensitivity is exceeded. The magnet then returns to it rest position. This device has minimal usefulness in a wood frame structure.

Perhaps the most successful technology used in detecting objects located behind concealing surfaces is the capacitive sensor/detector. This sensor works by detecting density changes in a wall and is therefore not limited to detecting only ferrous materials. The capacitive sensor can detect non-electrically conductive materials also. These capacitive finders can typically detect changes in wall density to a thickness of about three-quarters of an inch (19 mm). More advanced models have increased sensitivity to approximately a little more than an inch (26 mm). This detector does not work as well with thicker walls and does not provide a clear display of other objects behind the wall, such as pipes and wiring that are located more than approximately one inch (26 mm) away. Before driving a nail into a wallboard, it is important to know that the object obscured by the wallboard at that position is really a stud and is not a pipe.

Capacitive detector devices and methods have been provided with many different circuits used to implement them. There are, however, drawbacks to such devices one of which is that they are incremental in nature and the display they provide is not as desirable as many would want. They are referred to as being "incremental" because they use discrete capacitive components that are able to provide a detection area that is only as large as the capacitive component itself. Adding additional capacitive components has been attempted (see, for example, U.S. Pat. No. 6,198,271 to Heger et al.) but the cost and circuit complexity also undesirably increase. Providing greater and greater numbers of discrete capacitive detector devices or arrays of detectors in a single housing would cause the need for more wiring, more circuits, and more displays or display elements, all of which can increase the cost and size of a detector significantly.

Manual scans using a capacitive handheld device can take time to clearly locate a hidden stud. Furthermore, even when the device detects and displays a hidden object in the wall, the displayed shape does not visually persist as the device is moved along the wall toward or away from the hidden object. No real image of the entire object is provided, only incremental images of parts of the object are provided as the detector is moved along the obscuring surface. The viewer must then assemble these parts in his or her mind to "visualize" the entire object that is obscured. Thus another drawback in capacitive detector devices is the lack of persistence of the detected shape of a hidden object behind an obscuring surface.

U.S. Pat. Nos. 7,982,450 and 8,638,086 to Smoot describe devices and methods to provide an image of objects behind an obscuring, non-conducting surface using a capacitive detection approach. The disclosed devices and methods have provided a significant advance in the art and have solved a long-standing need for contractors, construction workers, and homeowners to be able to accurately visualize objects (studs, pipes, electrical wiring, etc.) behind obscuring wall surfaces. Yet further needs have been identified for providing a higher persistence of image, greater sensitivity of the detector, and for more economically providing a detector.

In regard to sensitivity, another factor in providing a successful detection and display device is the ability to penetrate far enough through the obscuring surface to detect and display as much as possible behind that surface; i.e., a device having increased sensitivity. Some walls are thicker than other walls. For example, walls constructed of lath and plaster are typically much thicker than the walls constructed of standard drywall materials. A lath and plaster wall may be 1.125" thick (2.86 cm) while a wall formed of wallboard may only be 0.5" thick (1.3 cm). Wallboard can vary from ½" (1.27 cm) to ⅝" (1.59 cm) depending on the type used.

Also, various building techniques can result in thicker walls. For example, soundproofing techniques can make the surface layer of a wall much thicker. In another soundproofing technique, a double wall is provided. In these cases, the pipes and electrical wiring are located even farther within the wall from the wall's surface. In such cases, the sensitivity of the detector would need to be higher in order to detect non-conductive objects located within such walls.

Hence, those skilled in the art have recognized a need for a capacitive detector device and method having a higher sensitivity for detecting objects located behind an obscuring surface, and to display an image of what is detected with a larger display area. A further need has been recognized for a capacitive detector device that provides an image of objects detected behind an obscuring surface, that image having a higher persistence level so that a more accurate picture of the detected objects may be visualized. Yet a further need has been recognized to more economically provide such a detector and display device. The invention satisfies these needs and others.

SUMMARY OF THE INVENTION

Briefly and in general terms, there is provided a system and method for detecting and displaying objects that are hidden behind an obscuring surface. In particular, in one aspect there is provided a device for detecting and displaying an object hidden behind an obscuring surface, the hidden object having a dielectric constant, the detecting and displaying device comprising an energy source, an electrode connected to the energy source, a chamber disposed between the electrode and the obscuring surface comprising a visual display material disposed in the chamber between the electrode and the hidden object, the visual display material having a visual display characteristic that is varied in response to the amount of energy applied to it by the electrode and in response to the dielectric constant of the hidden object, a motor having a rotating axle, the axle being connected to the chamber such that rotation of the axle results in rotation of the chamber between the electrode and the obscuring surface, a display area through which the visual display characteristic of the visual display material can be seen, and a motor controller programmed to control the motor to rotate the axle at a rate that is the persistence of vision rate of a viewer of the display area, wherein a change in capacitance caused by the hidden object is detected by the visual display material and the shape of the hidden object is displayed in the display area of the chamber by the varying of the visual display characteristic of the display material whereby the visual display material is used to both detect and display the hidden object.

In other aspects the motor axle is positioned through the electrode and the motor axle rotates the chamber in a full circle between the electrode and the obscuring surface. The visual display material comprises a luminescent gas, an in another aspect that luminescent gas comprises an inert gas. The display area through which the visual display characteristic of the visual display material can be seen comprises the electrode.

In other aspects, the motor axle is positioned outside the electrode and the motor controller is programmed to control the motor axle to move the chamber reciprocally through a selected arc that is less than a full circle, wherein the electrode has a size that covers the entire selected arc.

In method aspects in accordance with the invention, a method is provided for detecting and displaying an object hidden behind an obscuring surface, the hidden object having a dielectric constant, the method comprising rotating a chamber disposed between an electrode and the obscuring surface, the chamber containing a visual display material having a visual display characteristic that is varied in response to the amount of energy applied to it by the electrode and in response to the dielectric constant of the hidden object, applying energy to the electrode as the chamber is rotating and detecting capacitance of the hidden object behind the obscuring surface with the visual display material, displaying the visual display characteristic of the visual display material as it is being rotated and as it is detecting the capacitance of the hidden object, controlling the speed of rotation of the chamber to be at the persistence of vision speed of a viewer of the displayed visual display characteristic, wherein a change in capacitance caused by the hidden object is detected by the visual display material and the shape of the hidden object is displayed, whereby the visual display material is used to both detect and display the hidden object.

In yet other more detailed method aspects, the step of rotating a chamber comprises rotating the chamber about a position located through the electrode. The step of rotating the chamber about a position located through the electrode further comprises rotating the chamber in a full circle between the electrode and the obscuring surface. The step of rotating a chamber between an electrode and the obscuring surface comprises rotating a chamber containing a luminescent gas. The step of rotating a chamber containing a luminescent gas comprises rotating a chamber containing an inert gas.

In accordance with further aspects of the invention there is provided a device for detecting and displaying an object hidden behind an obscuring surface, the hidden object having a dielectric constant, the detecting and displaying device comprising an energy source, an electrode pad having a first surface configured to face away from the obscuring surface, the electrode pad also having a second surface configured to face toward the obscuring surface, a motor having a rotation axle, a strut having a proximal end and a distal end, wherein the strut is attached to the rotation axle of the motor at its proximal end and is configured to rotate with the rotation of the axle, wherein the electrode pad is located at the strut at a position outward from the proximal end of the strut whereby the electrode pad rotates with the strut, a capacitance detector connected with the electrode that measures a level of capacitance at the position of the electrode pad through the obscuring surface and the hidden object and provides a capacitance level signal representative of the capacitance measured during rotation of the electrode pad through the obscuring surface and through the hidden object, a visual display device disposed at the second surface of the electrode, the display device configured to provide illumination in real time based on receipt of the capacitance level signal, a motor controller configured to control the motor to rotate the rotation axle thereby rotating the strut and the electrode pad through a selected rotation area at a rate at a persistence-of-vision speed of a viewer to provide a visually continuous display by the visual display device throughout the rotation of the electrode pad, whereby the visual display device provides a more accurate visual display of the hidden object and its location due to the visual display device being co-located with the electrode that measures the capacitance of the hidden object.

In more detailed aspects, the visual display device comprises a plurality of light sources each having an intensity controlled by the capacitance level signal. In another aspect, the device for detecting and displaying an object hidden behind an obscuring surface further comprises a plurality of electrode pads located at the strut. The visual display device located at the electrode pad comprises a light redirecting device to redirect received illumination that is based on receipt of the capacitance level signal away from the obscuring surface, further comprising an illuminating device located separately from the strut and electrode pad, the illuminating device providing illumination representative of the shape of the hidden object in response to the capacitance level signal, and a light conductor configured to conduct the illumination representative of the shape of the hidden object to the visual display light redirecting device located on the electrode pad whereby the light redirecting device located at an electrode pad provides a more accurate visual display of the hidden object and its location due to being co-located with the electrode that measures the capacitance of the hidden object.

In yet other more detailed aspects, the device for detecting and displaying an object hidden behind an obscuring surface further comprises an energy control circuit configured to control the application of energy to the electrode from the energy source to expand or contract a depth of view of the electrode and the visual display material combination. The visual display device comprises an angled light diffuser. The motor controller is programmed to rotate the rotation axle reciprocally through a selected arc that is less than a full circle.

Additional aspects in accordance with the invention include a device for detecting and displaying an object hidden behind an obscuring surface, the hidden object having a dielectric constant, the detecting and displaying device comprising an energy source, an electrode connected to the energy source, a plurality of individual chambers grouped together into a physical planar array, the array of chambers being disposed between the electrode and the obscuring surface, the chambers being arranged so that they are not electrically connected with one another, the array comprising a visual display material disposed in each of the chambers between the electrode and the hidden object, the visual display material having a visual display characteristic that is varied in response to the amount of energy applied to it by the electrode and in response to the dielectric constant of the hidden object, a first planar array side configured to face the electrode, and a second planar array side configured to face towards the obscuring surface, a display area through which the visual display characteristic of the visual display material can be seen, wherein a change in capacitance caused by the hidden object is detected by the visual display material and the shape of the hidden object is displayed in the display area of the array of chambers by the varying of the visual display characteristic of the display material whereby the visual display material is used to both detect and display the hidden object.

More detailed aspects include a sensitivity enhancement device located at the second side of the planar array facing the obscuring surface, the sensitivity enhancement device comprising an array of metallic electrodes, whereby the metallic electrodes direct and intensify electric fields from the energy source traversing the electrode and planar array to increase sensitivity and penetrating depth through the obscuring surface. The sensitivity enhancement device comprises an electrically non-conductive substrate on which are located the array of metallic electrodes.

Other aspects include a controller circuit configured to control the application of energy to the electrode from the energy source to expand or contract a depth of view of the electrode and the visual display material combination. The display area through which the visual display characteristic of the visual display material can be seen comprises the electrode. The device for detecting and displaying also comprises a guard ring located about the electrode, the guard ring connected to the energy source wherein the guard ring shields the electrode, whereby electric fringing effects that would otherwise occur at the periphery of the electrode are inhibited. The visual display material comprises a luminescent gas which is in one aspect, an inert gas. The device for detecting and displaying further comprises a controller circuit that controls the energy applied to the gas to maintain the gas substantially near an ionization level at which the gas is just ionized to result in a glow of the gas. The controller circuit comprises a photo-detector that monitors the amount of light emitted by the gas and controls the energy applied to the gas so that the detected light remains just at the glowing stage. The controller circuit comprises a photo-detector configured to detect light emitted by the gas but not detect ambient light. The controller circuit performs a synchronous detection of the emitted light from the luminescent gas, the controller circuit comprising a photo-detector that detects the light emitted by the luminescent gas and provides a detection signal, wherein the energy source produces an electrode signal to drive the electrode, and the controller circuit further comprising a multiplier that multiplies the electrode signal by the detection signal with any resulting DC term fed back to the energy source, wherein the energy source is responsive to the fed back DC term to control the energy application. The electrode is configured to receive energy from the energy source and impress a relatively high voltage electric field across the luminescent gas to control ionization of the gas and brightness of display.

In an additional aspect, the device for detecting and displaying an object hidden behind an obscuring surface further comprises a phosphorescent sheet having a selected persistence characteristic, wherein the phosphorescent sheet is adapted to be placed over the obscuring surface and accept the electrode to scan the obscuring surface over the phosphorescent sheet, wherein the phosphorescent sheet is further configured to be activated by the illumination of the illuminating display device to present a display of objects located behind the obscuring surface covered by the phosphorescent sheet as the electrode is scanned over different parts of the phosphorescent sheet.

The electrode comprises a metal sensor pad. The visual display is a light-emitting diode. In further more detailed aspects, the motor further comprises a pulley mechanically coupled to the electrode and providing rotational movement to the electrode. The pulley has a hollow shaft, a luminescent device controlled by the capacitance detection circuit that is positioned remotely to the visual display, the luminescent device having a luminance that varies in response to a change in capacitance caused by the hidden object, and a specular reflecting surface is disposed within the hollow shaft of the pulley, the specular reflecting surface is positioned to reflect the light emitted from the luminescent device towards the visual display, wherein the visual display is a diffuse reflecting surface, the luminance of the diffuse reflecting surface changing in response to the varying intensity of light reflected from the specular reflecting surface. The specular reflecting surface has an angle of reflection of 45 degrees.

These and other aspects, features, and advantages of the present invention will become apparent from the following detailed description of the preferred embodiments which, taken in conjunction with the accompanying drawings, illustrate by way of example the principles of the invention.

DETAILED DESCRIPTION OF PREFERRED EMBODIMENTS

Figure 1:
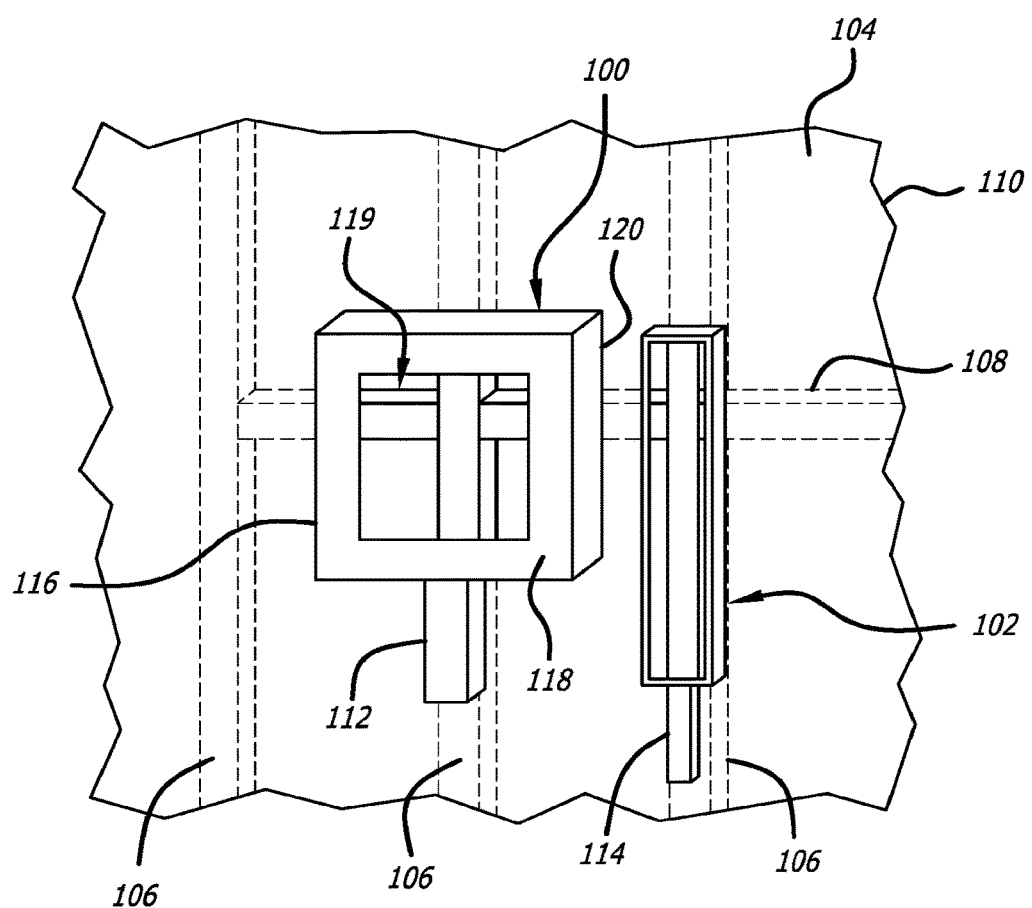
FIG. 1 illustrates two embodiments of a capacitive detector arranged in accordance with the inventions of U.S. Pat. Nos. 7,982,450 and 8,638,086 to Smoot. Both detector embodiments are placed on an obscuring wallboard surface to detect objects located behind that wallboard which in this case are wall studs and cross braces. Both embodiments have frames each of which has a handle. A luminescent gas is located within the frame between and electrode and the wallboard surface and therefore forms a part of the capacitive detection circuit. Because it is a luminescent gas, it also presents a display of the obscured objects detected behind the wallboard.

Referring now in more detail to the exemplary drawings for purposes of illustrating embodiments of the invention, wherein like reference numerals designate corresponding or like elements among the several views, there is shown in FIG. 1 two detector devices 100 and 102, both of which are configured and operate in accordance with aspects of the invention. Both are located over a surface 104 that is obscuring the existence of objects (shown in dashed lines) located on the other side of the surface. In this example, the obscuring surface is a wall 110 and the hidden objects located behind or within the wall comprise three vertical studs 106 and three horizontal cross braces 108. The detector devices 100 and 102, sometimes referred to as scanners, are being used to scan the surface 104 of a wall 110 to reveal structures 119, lying below or behind the surface. The first detector 100 is square in this embodiment and provides a larger view of the objects 106 and 108 that are obscured from view by the wall 110. This first detector includes a handle 112 for ease in use. The second detector 102 is more in the shape of a wand having more of an elongated shape with one dimension being much longer than the other. This second detector also comprises a handle 114 for ease of use.

Referring to FIG. 1 further, the detector device 100 on the left includes a housing 116 to which the handle 112 is attached. A user may grasp the handle and move the detector device in any direction the user chooses along the wall surface 104. This can include up or down, left or right, or diagonally or in any other direction or series of directions. Although shown in other drawings and described in much more detail below, the housing includes an electrode and, in accordance with one aspect of the invention, a display device. In one embodiment, the electrode is transparent and is located over the display device. The arrangement is such that the front 118 of the housing faces the user and the back 120 of the housing is put into contact with the obscuring surface 104 by the user. The electrode is located towards the front of the detector (towards the user) while the display device is located between the electrode and the back of the housing. Thus the display device is positioned to be a part of the capacitive detection circuit of the detector device 100 in that the electrode energy will be applied through the display device to the obscuring surface and then into the wall, as is shown in other figures and is described below.

In another embodiment, the detector device 100 includes a display device and an electrode wherein the display device is not part of the capacitive circuit but is controlled by a processor to simultaneously display the hidden objects behind the wall 110 as they are detected by the capacitive circuit of which the electrode forms a part. In this embodiment, an electrical parameter of the electrode is monitored and processed to result in the control signals for the display device. In one embodiment, the current flow of the electrode is monitored to produce the display device control signals because the electrode current flow changes in accordance with the capacitance presented by the wall and the hidden objects behind the wall.

Figure 2:
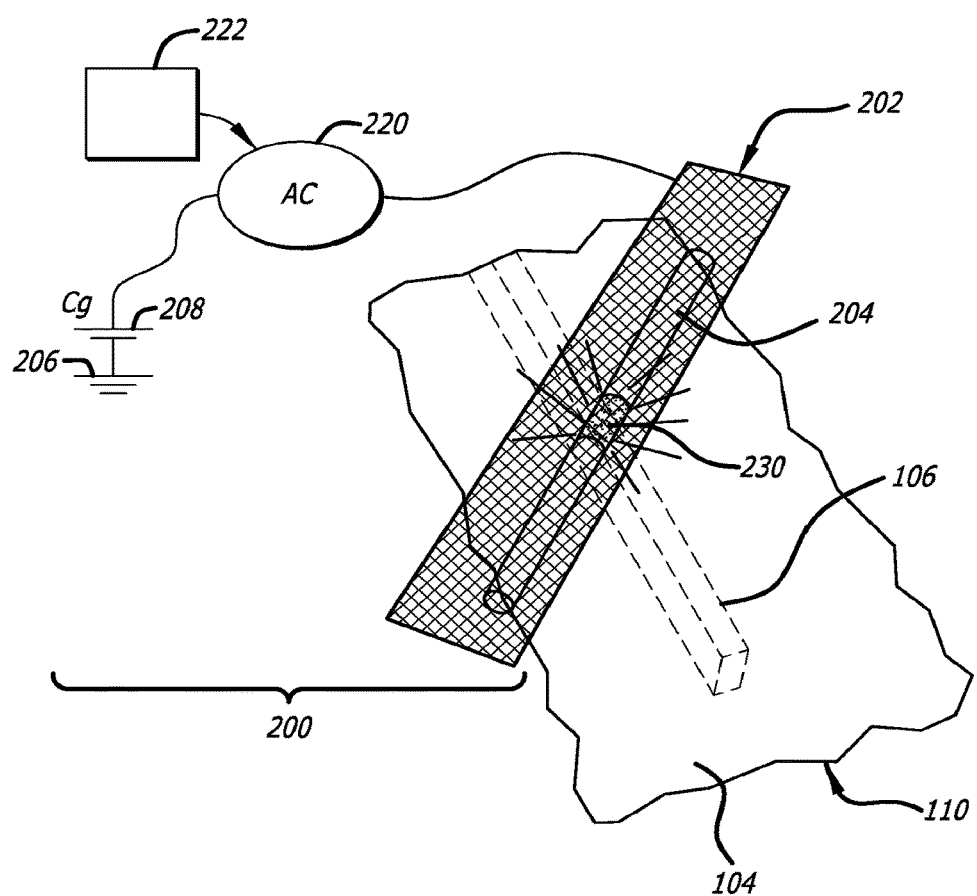
FIG. 2 presents a schematic view of the use of a chamber containing luminescent gas disposed between a transparent electrode screen and the hidden object within a wall surface, an AC energy source being connected with the electrode to control the ionization of the gas in the chamber to detect and display the hidden object.

Referring now to FIG. 2 a first embodiment (linear) of a detector device 200 in accordance with aspects of the invention is shown. This detector device resembles the "wand" or elongated type of detector 102 shown in FIG. 1 in that one dimension is much longer than the other. In this embodiment, the detector employs a rectangular, transparent, conductive electrode 202 which is mounted above a transparent cylindrical gas tube 204. The electrode 202 is substantially transparent. A wire mesh material or an indium-tin oxide coated glass sheet are suitable for the application. In one embodiment, the electrode comprised electrically conductive window-screen type material.

The transparent gas tube 204 contains a luminescent gas under low pressure. The noble gasses such as neon, argon, and krypton (or mixtures of them with other gasses) are suitable for the application.

A source of high frequency, high voltage alternating current 220 is applied to the electrode 202. This voltage is applied with respect to ground 206 in this case. When the inventive detector device 200 derives its power from a mains supply, this ground may be obtained via direct connection to the ground lead of its three conductor power cable, or a capacitive connection 208 to ground can be obtained through the use of a small-valued capacitor Cg (100 pf or so) connected between the ground side of the high voltage AC supply 220 and the ground lead of the three conductor power cable (not shown in the figure). Even in cases where the detector device is battery powered, a "dummy" three terminal power plug, with connection only to the ground pin, can be employed, and a wire brought from this ground pin into the detector device to supply the described ground.

In another embodiment, the detector 200 can be battery-powered, handheld, and without an umbilical cord, and in that case, the capacitance of the user to ground, and to areas of the circuitry, even though an (ideally plastic) electrically insulating mounting case is used, will be sufficient to provide a return path for currents to flow through the gas 204. A handle and case (not shown in this view) are provided to allow the AC source 220, electrode 202, and the gas tube 204, to be held up to the wall 110 and scanned over its obscuring surface 104 as a combined unit. In operation, as the handheld detector device 200 of FIG. 2 is scanned over a wall surface 104, the gas inside the tube 204 will glow at the locations where there is an object or a portion of an object. As shown in FIG. 2 in this case, the gas tube 204 is glowing 230 over the wall stud 106 obscured by the surface 104 of the wall 110. By increasing the voltage or the frequency of the power source 220 through a controller 222, thereby increasing the capacitive current flow applied to the electrode 204, the depth of surface penetration of the detector device can be controlled. For example, while wall studs may be in contact with the inner surface of a wallboard, wiring or pipes may be farther away from the outer surface 104 and inner surface of a wallboard. Increasing the capacitive current flow to the electrode will enable its detection range to extend farther into the obscured volume behind the wall 110.

Figure 3A:
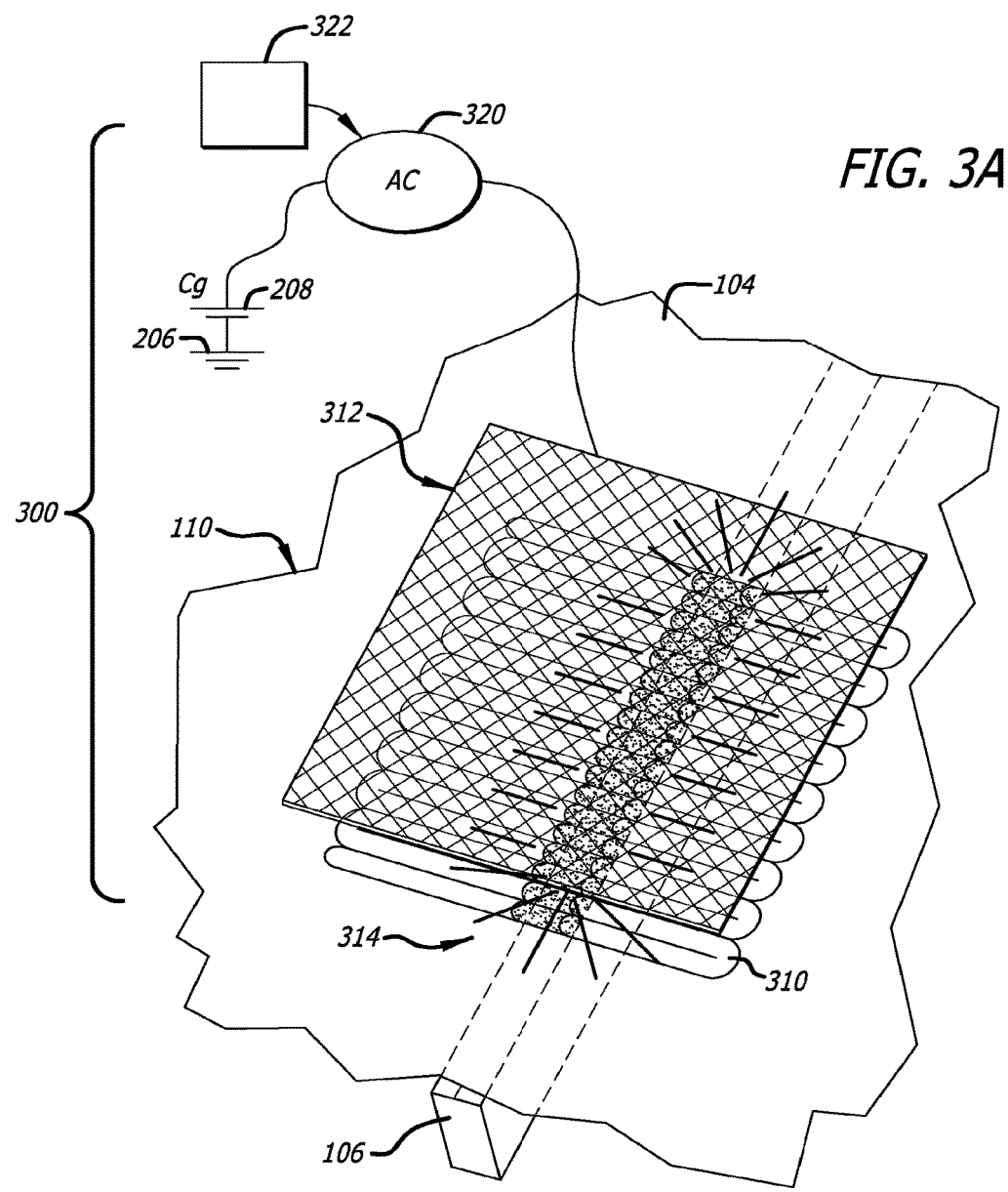
FIG. 3A is a schematic view similar to FIG. 2 but in this embodiment, a serpentine-shaped chamber of luminescent gas is used that will provide a greater surface area under the obscuring surface for viewing, with a single transparent electrode screen used to control the energy applied to the gas.

In another embodiment depicted in schematic form in FIG. 3A, a different configuration of a detector device 300 is shown. Instead of the single linear strip of incremental detection capability shown in FIG. 2, FIG. 3A provides a detector device and method capable of examining large, two-dimensional areas of wall surface 104. The detection device 300 illustrated in FIG. 3A comprises a serpentine gas tube 310 which in this embodiment is ideally a clear, sealed, neon tube similar to commercial neon lighting tubes, but without end electrodes, a planar, electrically-conductive and optically transparent electrode sheet material 312, which is mounted directly above (with respect to the obscuring wall surface 104 and the gas tube 310), and a high frequency AC voltage source 320 which is connected to the electrode sheet 312. As in FIG. 2, the AC voltage source includes a controller 322 that is used to control the voltage or frequency of the power source 320.

In accordance with the embodiment of FIG. 3A, the user views the serpentine gas tube 310, and the wall surface 104, through the transparent electrode sheet 312. The novel detector device 300 can also be outfitted with a non-conductive housing and a handle (such as the handle 112 shown in FIG. 1 for example) to hold the assembly in alignment as a unit. The gas in the tube 310 will illuminate in areas 314 where it is over objects such as a stud 106 behind the wall 110.

Figure 3B:
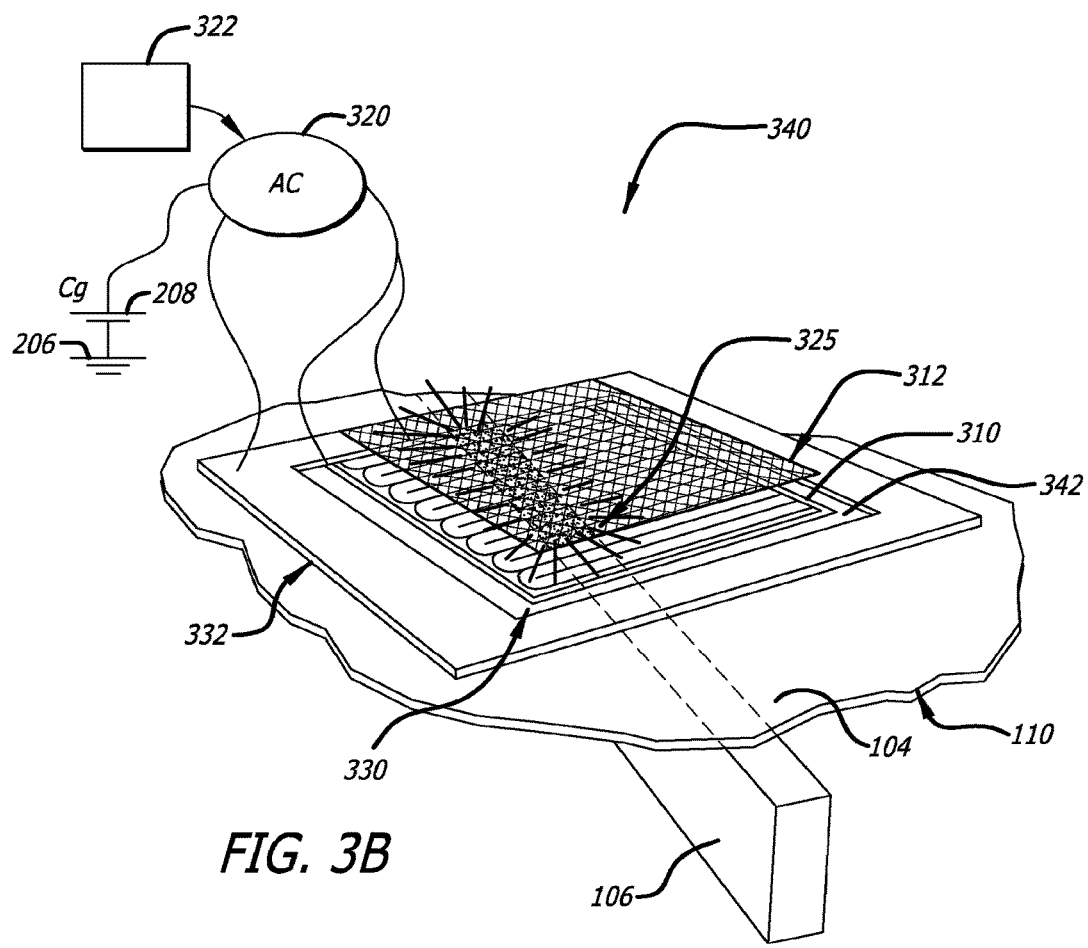
FIG. 3B is a variation of the embodiment of FIG. 3A in which a guard ring is disposed about the electrode to control fringing effects of the electrode that ionizes the gas in the chamber, and a ground ring is disposed about the guard ring to provide a return for the energy source at the site of the device.

Yet another embodiment is shown in FIG. 3B where the use of an in-plane guard ring 330 and an in-plane ground ring 332 are shown as part of the detector device 340. Here, a rectangular transparent substrate 342 (a transparent acrylic sheet would be suitable) provides a base for the detector device 340. A serpentine gas tube 310 sits atop this substrate with an electrode 312 above that. As in FIG. 3A, the electrode in this case comprises an optically transparent electrode sheet material 312. Surrounding the electrode is the ground ring 332 and positioned between the ground ring and the electrode 312 is the guard ring 330, which encircles the electrode and tube.

When the detector device 340 is placed against the wall surface 104, the ground ring 332 forms a capacitive connection to the wall surface 104, and thus provides a return for ground currents for the AC supply 320. Thus, the ground ring's 307 capacitance to ground can augment or replace the capacitance to ground of the user.

The guard ring 330 that surrounds the serpentine tube 315 is placed in closer proximity to its edges. This guard ring may be connected to the same lead of the high voltage source 320 that is used to drive the top electrode 312 of the detector device. This guard ring prevents electric fringing effects that would otherwise occur at the periphery of the gas tube electrode 312 to thereby shield the electrode. These fringing effects would tend to cause the field across the peripheral areas of gas tube 310 to be illuminated before portions located closer to the center were illuminated.

In accordance with aspects of the invention, to further increase the cost-effectiveness of a detector device, conventional cold cathode fluorescent lamps (CCFL) or other commercially available tubes, or sphere-shaped lights, can be used in an array to provide large detection surfaces of arbitrary aspect ratio. This different embodiment is presented in FIG. 3C. In this embodiment, a plurality of containers 350 of luminescent gas are positioned together to form a larger display of obscured objects detected behind a wall or other surface. Although the drawing numeral "350" is pointing to only one container, it is meant to include all of the twenty-one containers shown. Lead lines have been left off from the other twenty containers to preserve clarity of illustration. Although a single or continuous chamber of luminescent gas may be employed as a sensing and display system as is described above, it is cost advantageous to use an array of commercially-available linear, gas-filled tubes sold for decorative applications due to their low cost, and broad availability.

Figure 3C:
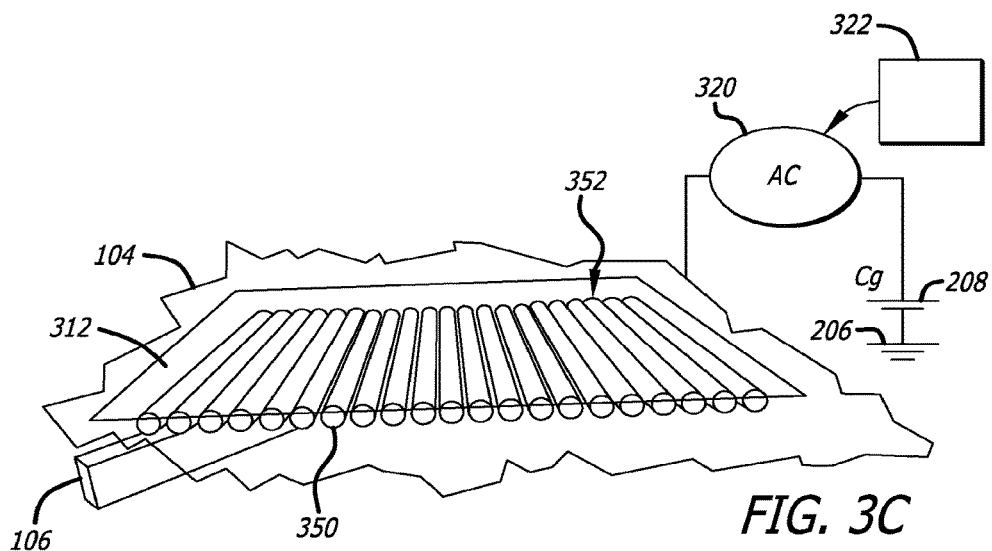
FIG. 3C is an embodiment of a device in accordance with aspects of the invention in which multiple containers of luminescent gas are positioned together to form a larger display of obscured objects detected behind a wall or other surface. A transparent electrode is positioned over the gas containers thereby making the gas in the containers part of the capacitive detection circuit for detecting the stud shown in the figure. A broken-away obscuring surface (wall) has been shown in schematic form between the gas containers and the stud for clarity of illustration.

FIG. 3C depicts the use of an array of separate tubes where each tube independently forms a portion of an overall detection and display surface. The inventor has found that miniature "cold cathode fluorescent lamps" ("CCFL") of diameters of 2-3 mm make excellent detector/display elements. Tubes such as those manufactured for decorative lighting and as liquid crystal display edge-lighting devices are rugged, small in diameter (allowing a large flow of current through the tubes when in the detection mode) and are widely available. For use in the inventive devices shown and described herein, the wires usually mounted at the ends of the tubes may be removed. Such tubes are available presently at Octopart, Inc., 43 West 24th St., Suite 12A, New York, N.Y. 10010 (https://octopart.com/parts/category—light-sources-and-emitters/current-rating—0.005/?p=2&c=4467).

A transparent electrode 312 is positioned over the gas containers 350 thereby making the gas in the containers part of the capacitive detection circuit for detecting the stud 106 shown in FIG. 3C. A broken-away obscuring surface (wall) 104 between the gas containers and the stud is shown in light lines for clarity of illustration. The same circuitry shown in FIGS. 3A and 3B is shown in FIG. 3C.

Figure 3D:
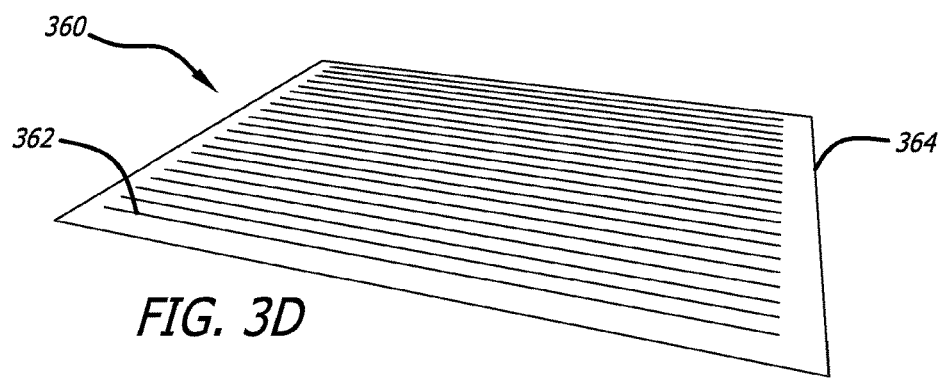
FIG. 3D presents an array of printed line conductors on an otherwise non-conductive substrate that provide sensitivity enhancement. The array is located as the lower layer of a detector; i.e., between the luminescent gas and the obscuring surface, to increase the sensitivity of the detector through the obscuring surface.

FIG. 3D presents a sensitivity enhancement device 360 comprising an array of printed line electrical conductors 362 on an otherwise non-electrically conductive substrate 364. This device provides sensitivity enhancement to a capacitive detector, such as those shown herein. Although the sensitivity of the detector systems shown and described herein is adequate in almost all cases, the inventor has found that the pattern or array 360 of metallic electrodes 362 as shown in FIG. 3D, placed on a thin, non-conductive, substrate 364 at the bottom side of the gas filled chamber(s), directs and intensifies the electric fields transiting the detector so that increased sensitivity and penetrating depth result. Although not intending to be bound by theory, it is believed that the electrodes concentrate the flux (strength of the electric field) in their local area (close to the bottom of the display tubes). It is this field that lights the local areas inside the luminescent tubes, thus strengthening the flux and therefore increasing the sensitivity of the detector device.

It is believed that the electrodes perform their function because their electrical permittivity is much higher than that of air, and as a result the lines of flux of the electric field tend to go through them (from the top electrode to ultimate ground inside the obscuring surface), rather than through the air (lower permittivity) around them. The effect is one of concentration.

Instead of lines of electrical conductors as shown in FIG. 3D, arrays 360 of electrical conductors may include other patterns for the electrical conductors. For example, arrays of electrical conductors may comprise dots, circles, or other shapes. The lines of electrical conductors, or electrodes illustrated in FIG. 3D is only one embodiment. Additionally, the substrate 364 may be formed of a clear, translucent, reflective, or opaque material as desired. Depending on the light source used to display the hidden objects, the substrate 364 coloring or surface characteristics may be selected to provide contrast enhancement or brightness enhancement of the light produced by the display device.

The array is located as the lower layer of a detector; i.e., it is positioned between the luminescent gas and the obscuring surface, to increase the sensitivity of the detector through the obscuring surface. As in the technique used in FIG. 3C with the drawing numeral 350, the drawing numeral "362" in FIG. 3D is pointing to only one electrically-conductive line but it is meant to include all twenty-one of the conductive lines shown. Lead lines have been left off from the other twenty conductors to preserve clarity of illustration.

Figure 3E:
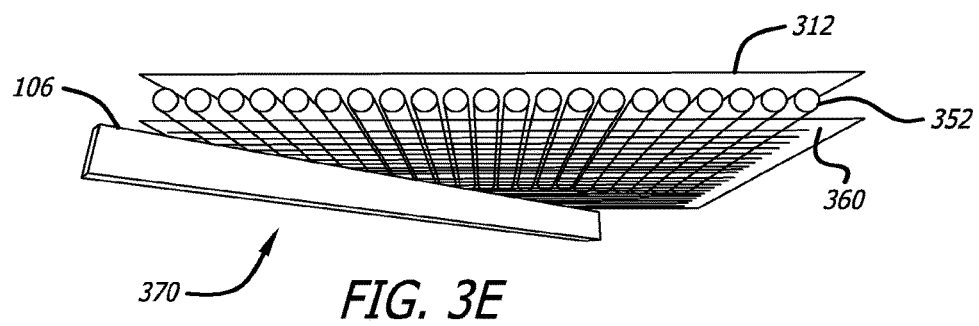
FIG. 3E is an embodiment combining the elements of FIG. 3C and FIG. 3D in accordance with aspects of the invention to show an assembly of the transparent electrode and the sensitivity enhancement device sandwiching the array of luminescent gas containers which in this embodiment are confined within a plurality of glass tubes to form a detector that may be held against an obscuring surface, such as a wall (not shown), to detect and display objects located behind the obscuring surface, such as the stud shown in the figure.

FIG. 3E is an embodiment that combines elements of FIGS. 3C and 3D in accordance with aspects of the invention. There is shown part of a detector assembly 370 in schematic form. That detector assembly comprises the transparent electrode 312, the sensitivity enhancement device 360, both of which are sandwiching the array of a plurality of glass tubes 352 between them. Each glass tube contains luminescent gas to form a display device 352. The detector 370 may be held against an obscuring surface such as a wall (not shown), to detect and display objects located behind the obscuring surface, such as the stud 106 shown in the figure.

Although not shown, a ground ring 332 and/or a guard ring 330 such as that shown in FIG. 3B, may be used with the embodiments of FIGS. 3C, 3D, and 3E. However, the lines of electrical conductors 362 shown in FIG. 3D would not be connected to the ground or guard rings but would be nested inside them.

Figure 4:
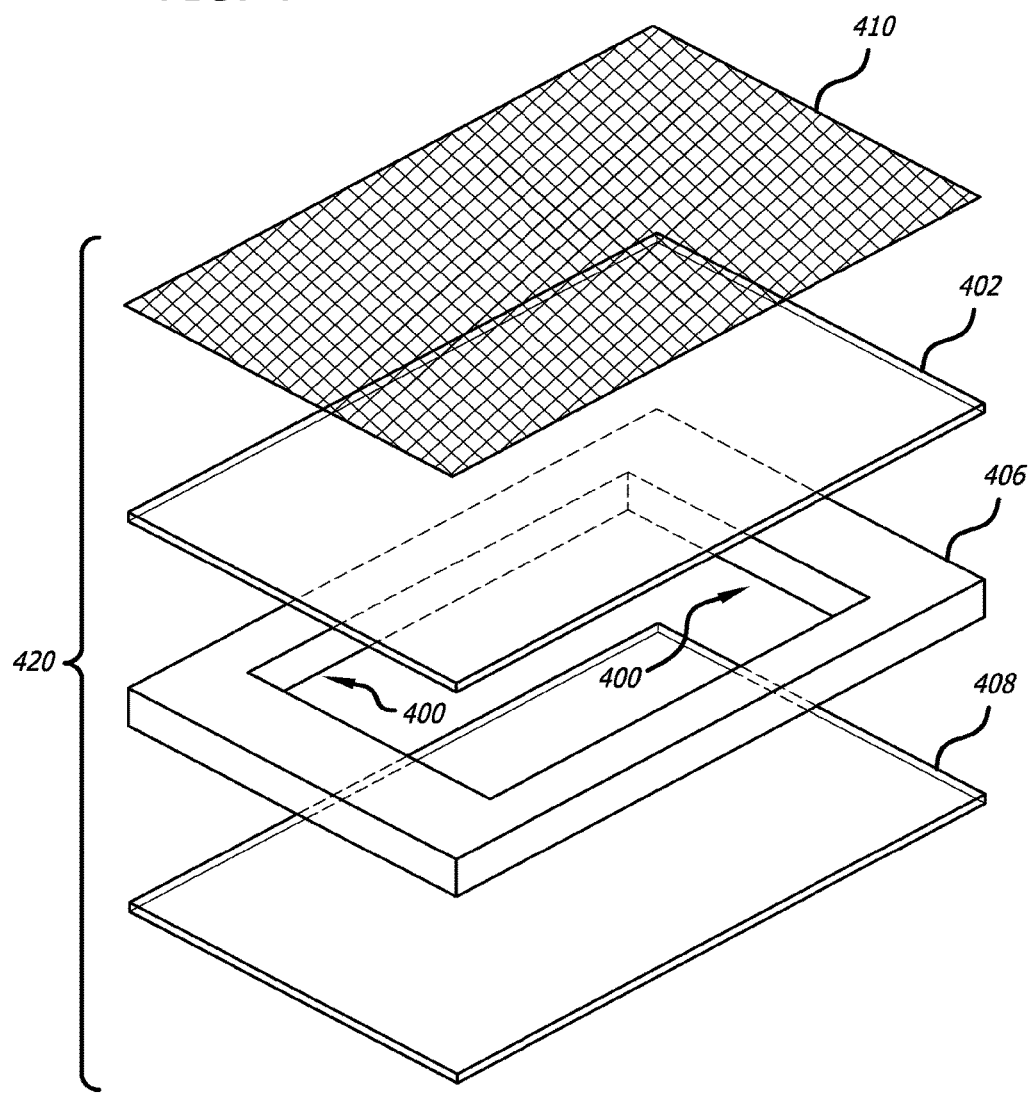
FIG. 4 shows the manufacture of a rectangular chamber with a built-in transparent electrode, the luminescent gas being disposed within the frame and transparent layers located on either side of the frame.

In a further embodiment as shown in an exploded form in FIG. 4, a rectangular evacuated chamber 400 is formed by means of the combination of a top optically transparent layer 402, an open rectangular frame 406, and a bottom optically transparent layer 408. The layers are hermetically bonded together and the chamber 400 formed thereby is filled with a luminescent gas. A top, visually-transparent, conductive electrode 410 is placed over the entire unit. This electrode may be a plated-on transparent coating applied to the top optically transparent layer 402 to form the detector device 420. A non-conductive case and handle (not shown) are provided for easy use in sliding the detector over a desired probe area. As in other embodiments, the detector device of FIG. 4 places a luminescent gas between an electrode and an area to be scanned with the gas forming a part of the detector circuit as well as simultaneously providing a visual display. The gas forms part of the capacitance link between the electrode and the ground and is thus directly affected by the capacitance of the obscuring surface and the hidden objects behind that obscuring surface since the electrical energy through the gas is a direct result of that capacitance.

It has been noticed during the course of developing the invention, that once an area of gas ionization occurs, the area tends to bloom past the location causing the initial ionization. In each of the inventive embodiments above, while it is desirable to have the device be as sensitive to under-surface objects as possible, it is also critical to limit the size of the glowing area so that it corresponds as closely as possible to the size and shape of the obscured object that is detected. To achieve this goal, it is important that the voltage applied across the luminescent gas in the evacuated chamber be adjusted to a point just supporting gas ionization; i.e., at ionization potential but not significantly higher. Then, even the slightest increase in capacitance in areas adjacent the detector device (causing the highest local AC potentials across sections of the gas) will ionize the gas directly above the detected object. In order to achieve this, the voltage, and ultimately current, delivered to the gas-filled chamber must be detected and regulated to keep the gas at this threshold point.

In each of the embodiments discussed below and shown in the figures, significant increases in high-voltage AC current occur as the electrode voltage increases and the gas begins to ionize, thus this current may be used in a feedback loop to control either the voltage, or frequency of the high-voltage such that the image achieved with the system is a true representation of the below-surface items. The high-voltage electrode current itself may be measured (for instance by using a small series resistor and sensing the current flow in it), or conveniently, since the high voltage will often be derived from a lower voltage supply voltage, by measuring the current being delivered by this lower voltage supply.

Figure 5:
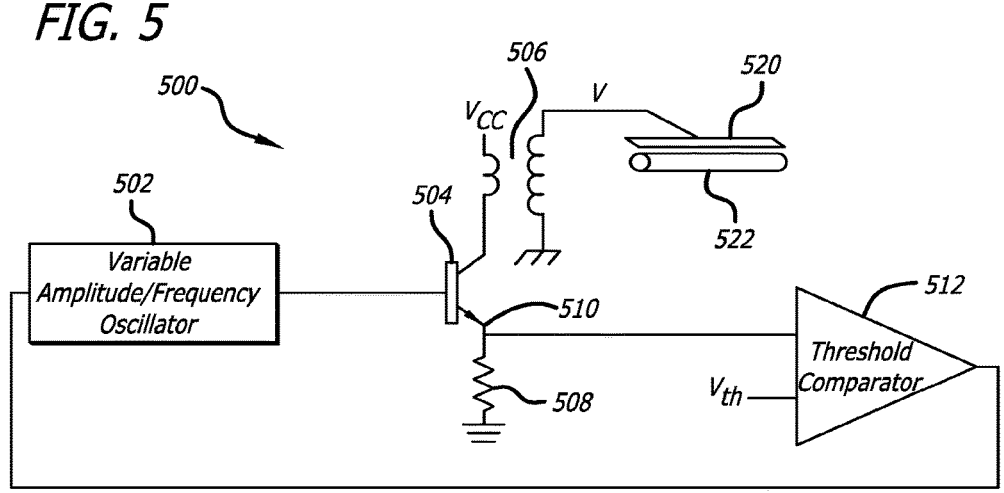
FIG. 5 presents an electrical diagram of the operation of control over the energy level of the luminescent gas in the chamber with the emitter of the semi-conductor device being monitored for current flow to thereby control the oscillator accordingly to keep the gas just at the ionization level so that it continuously glows.

FIG. 5 depicts this technique. Here, a power control circuit 500 includes a low voltage variable amplitude oscillator 502 that drives an output transistor 504. The transistor 504 in turn drives a step-up transformer 506. The transformer 506 will be of the high-turns-ratio type useful for generating high AC voltages. The output of the transformer is used to provide power to the top electrode 520 above the gas tube 522. The instantaneous drive currents of the transistor 504 are monitored through the use of a current sense resistor 508 in its emitter lead 510, and compared to a (adjustable or fixed) threshold Vth via a comparator/feedback amplifier 512. Increases in drive current are used as negative feedback and regulate the variable amplitude oscillator 502 so that the overall amplitude of the high voltage signal "V" applied to the transparent electrode 520 may be kept just above the ionization threshold of the gas chambers 522 in each of the above-described detection embodiments.

In a related manner, the oscillator 502 may be used in a constant amplitude variable frequency mode. In this case, the feedback loop regulates the frequency of the oscillator. Since higher frequencies cause more current through a fixed capacitance, the loop 500 lowers the frequency when the gas begins to ionize and raises it when the gas is below its ionization point. It should be noted that pulse width modulation control may also be used to keep the gas just on the edge of conduction in each of the regulating means.

Figure 6:
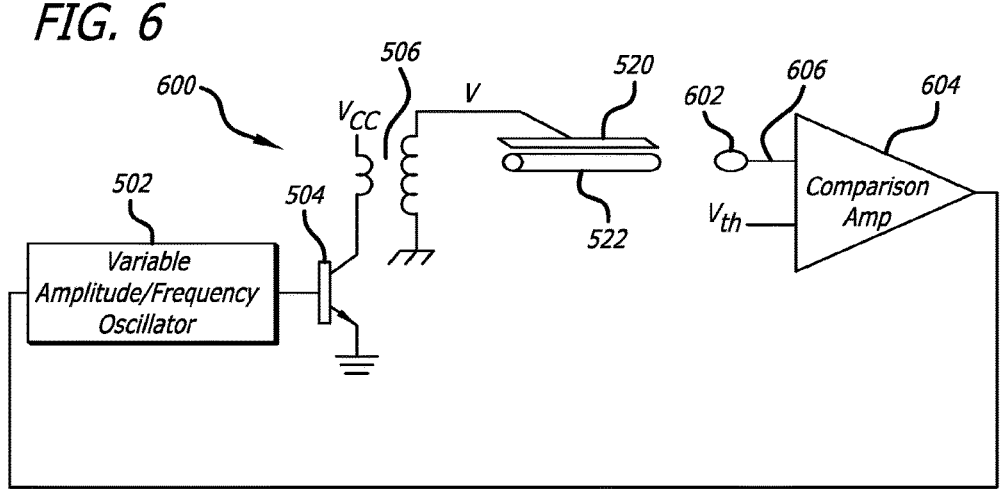
FIG. 6 is another embodiment of control over the ionization of the luminescent gas in this case by using a photo-detector to actually measure light output of the gas, compare it to a predetermined threshold level voltage and to control the oscillator to keep the gas just at the ionization level.

An alternate method of keeping the gas in the chamber just at the point of ionization is to monitor the light generated by the gas as it just begins to ionize. To achieve this goal, the circuit 600 of FIG. 6 may be employed. In this circuit, the low voltage variable amplitude oscillator 502 drives the output transistor 504. The transistor 504 in turn drives the step-up transformer 506 and generates the high voltage AC signal V ultimately applied across the luminescent gas in the chamber 522. An optical detector 602 detects light emitted by the gas 522. The optical detector 602 is illustratively a photocell sensitive to the wavelength of light emitted by the luminescent gas, although several other devices may be used to detect this light including photodiodes, phototransistors, and others. A comparison amplifier 604, with an adjustable threshold voltage "Vth" provides the feedback mechanism. In operation, when the overall device 600 is turned on, the AC voltage level V at the electrode 520 ramps up since there is no light coming from the gas tube 522. At some point, V will reach the ionization point of the gas (at the location where this ionization point is the lowest) and the gas will start to glow. When the first glow occurs, the photo-detector 602 detects this light and applies its signal 606 to the threshold comparator 604. As the amount by which this signal 606 exceeds the threshold Vth increases, the voltage at the output of the comparator 604 causes the amplitude or frequency of the variable amplitude oscillator 502 to decrease. This negative feedback curtails the current caused by V at the electrode 520. As a result of this feedback process, the gas-filled tube reaches a low steady state glow level and is set for maximum sensitivity. As the detector device is placed against a wall to be probed, the system will constantly adjust itself so that only items with a relatively higher capacitance to ground cause specific parts of the gas in the chamber 522 to glow.

Figure 7:
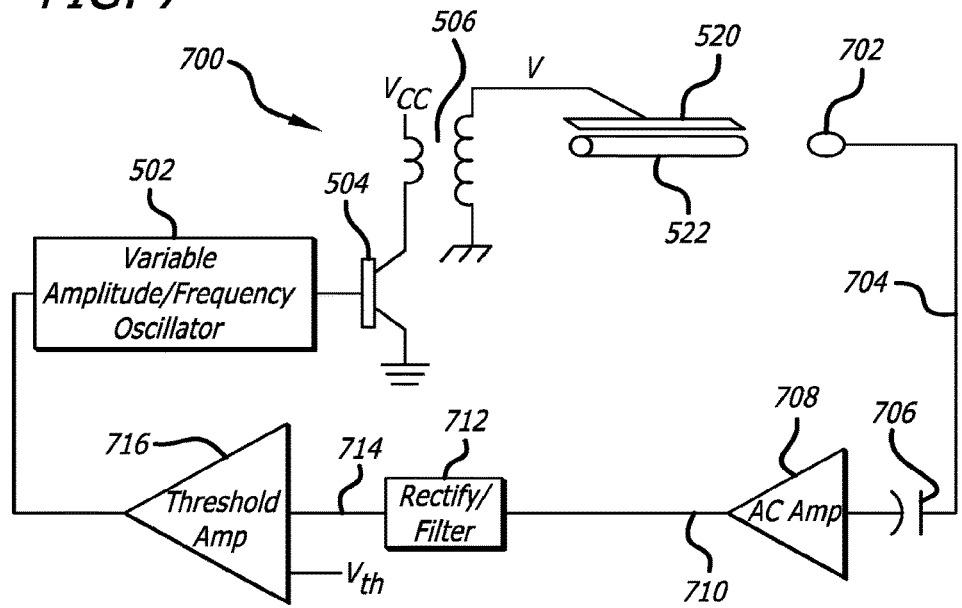
FIG. 7 provides yet a further view of a circuit used to control the light output of the luminescent gas in the case where ambient light may adversely affect the circuit of FIG. 6. In this circuit, the light output of the luminescent gas is sensed, any DC component in the resulting signal is blocked, and the resulting signal is amplified, filtered, and rectified, and again compared with a threshold level voltage to control the oscillator to keep the gas just at the ionization level.

In cases where outside, extraneous, or ambient light might interfere with the sensing of light in the gas-filled chamber 522, the circuit 700 exemplified by FIG. 7 can be used. Analogous components of this circuit are as described earlier. Here, the AC component of light coming from the tube 522 is detected by a high frequency capable photodetector 702. This signal 704 is received by a DC blocking capacitor 706 and then amplified by an AC coupled high frequency amplifier 708. The amplified signal 710 is then applied to a rectifier/filter 712. The frequency response of the amplifier 708 is set so that the multi-kHz frequencies of the light emitted by the gas chamber 522 is passed, but not ambient light from, for instance, fluorescent bulbs which will be predominately at much lower frequencies. The rectified and filtered output signal 714 is applied to a threshold amplifier 716. The threshold voltage Vth of the threshold amplifier 716 is adjusted so that the output of the threshold amplifier 716 keeps the high voltage signal "V" at a level insuring greatest contrast and sensitivity for the overall detector device.

Similar to the previous embodiment shown in FIG. 7 in cases where outside light would tend to interfere with the device's ability to discern the level of light being generated by the gas chamber, detection of the AC portion of the light is employed. In order to have even greater immunity to outside ambient light, a synchronous detection technique may be used.

Figure 8:
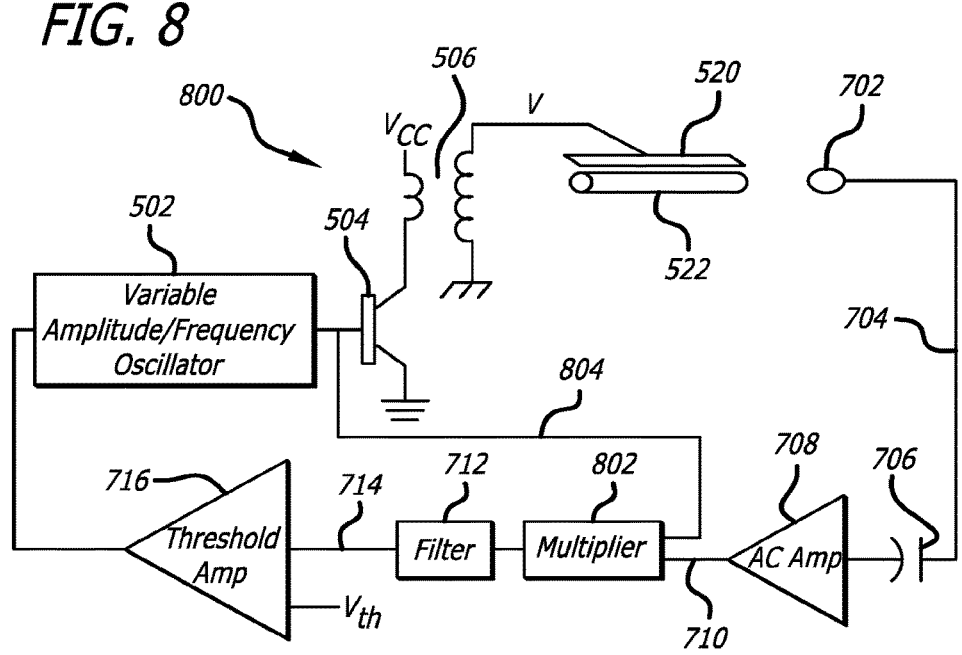
FIG. 8 provides a circuit that may be used in the case where outside light would interfere with the ability to measure the illumination provided by the luminescent gas, in which the output of the oscillator and the output of the luminescent gas sensor are multiplied together to result in a DC term that is used to control the ionization of the gas.

In the case of FIG. 8, the circuit 800 uses an oscillator 502 not only to drive the high-voltage circuitry for producing the HVAC signal, but its oscillator output signal 804 is also applied to a multiplier circuit 802. The oscillator signal 804 is multiplied by the AC amplified signal 710 coming from the photo-detector 702. As is known in the art, if two signals having the same phase and frequency are multiplied, the resultant will contain a DC term representative of the amplitude of the input AC signal. This filtered DC term is applied to a comparator amplifier circuit 716 and provides an interference free feedback signal for the oscillator 502.

Figure 9:
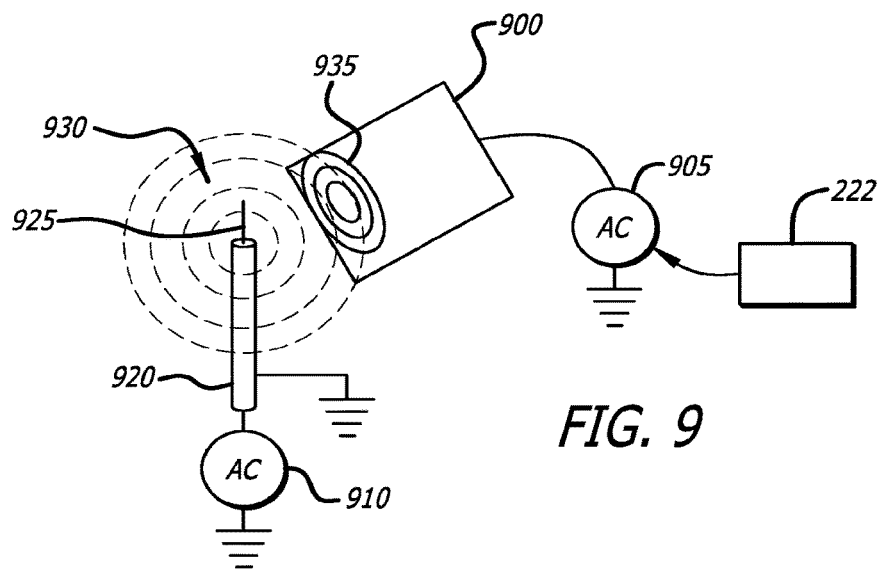
FIG. 9 provides a view of a gas ionization detector device in accordance with aspects of the invention in which the existence of an electromagnetic radiation source is detected and mapped.

FIG. 9 illustrates an embodiment of an inventive detection device 900 being used to detect the presence and strength of electromagnetic fields. A source of AC voltage 910 is connected through shielded wire 920 to a point emitter 925. The point emitter 925 radiates a varying electric field with equi-potential lines 930. The detection device 900 is brought near the emanating field and the field is detected as a gray scale area image 935 where higher potentials glow more or less brightly than areas of lesser potential. If the AC power source 905 providing excitation for the detection device 900 is adjusted to be a few Hertz displaced or "offset" from the frequency of the AC source 910 of the point emitter 925, a beat frequency will be set up such that the image viewed on the detector device 900 will flash or blink at the beat frequency since the two fields will alternately augment or diminish the voltage across the gas in the detector device 900.

The use of the detector device 900 in this manner is helpful for the purpose, for example, of determining the point of origin of stray electric fields. Since stray fields in electronic equipment can cause interference, crosstalk, and general malfunction, the detection 900 in accordance with the invention can be used to locate these fields, and having located them, visually evaluate the effect of various approaches to mitigate them.

Figure 10:
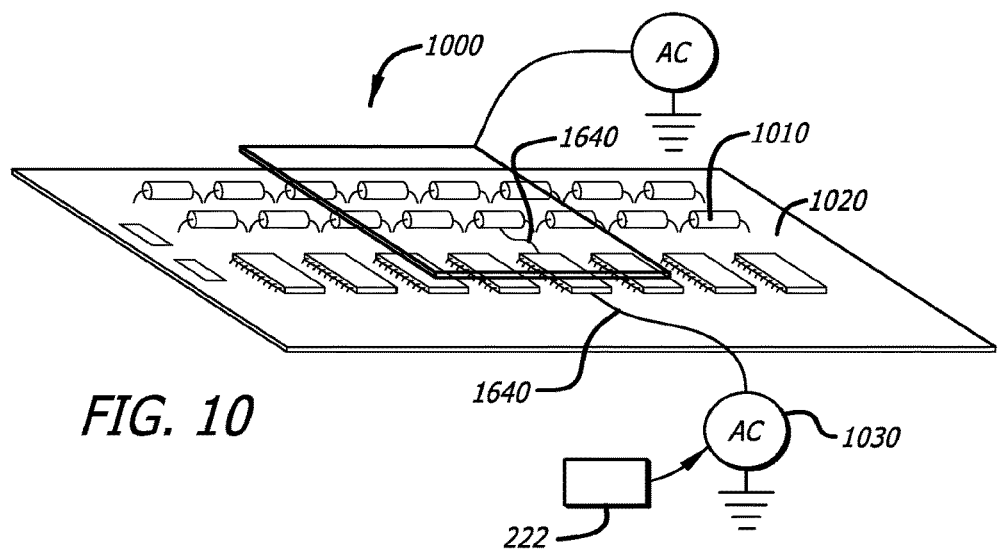
FIG. 10 shows the use of a gas ionization detector device configured in accordance with the invention to detect electrical connections between components on an integrated circuit board.

FIG. 10 shows the use of a detector device 1000 in accordance with aspects of the invention, to inspect the connectivity of, for instance, electronic components 1010 on a circuit board 1020. Those components that are connected to an AC source 1030 via intact paths 1040 on the circuit board will cause a flashing pattern on the screen of the detector device 1000. Indeed, different frequencies can be used to provide different flashing patterns for different paths on circuit boards. Thus, large areas of electronic devices can be scanned quickly and efficiently in broad swathes for connectivity of individual components, or for unintended short circuits between components.

Such detection of intact paths is useful, for example, to verify whether circuit boards have been manufactured properly, or to trace the location of breaks in connectivity in order to repair a circuit board which is functioning incorrectly. Additionally, the use of flashing displays as discussed above can be extremely helpful in low sight situations or in situations with the shade of one object on the screen is only slightly different from another object.

In the case of the luminescent tube versions of the detection system, the screen (array of tubes) can be covered with a transparent optical filter that selectively passes the light generated by the tubes (for instance blue light) and rejects light of other colors. This increases the contrast of the displayed image.

In addition, a so-called privacy screen (micro-louver material manufactured by 3M) can be additionally or alternatively layered over the tubes. These films are essentially miniature Venetian blinds and preferentially pass light in a particular direction (set to be towards the user's eyes) and will shut out light, from, for instance, overhead fluorescent lights.

The above-described detection devices use evacuated chambers filled with luminescent gases that emit light when an appropriately high voltage electric field is impressed across them. The luminescent gas chambers are brought into close proximity with a wall surface. One terminal of a high voltage, low current capability, alternating current voltage supply is applied via a transparent electrode (wire mesh often suffices) to the side of the luminescent gas chamber away from the wall surface. The other terminal of the relatively high AC voltage is applied either directly to ground, or is capacitively coupled through the user's body to ground, or may have a path to ground through a ground ring surrounding the chamber and transparent electrode. The AC voltage is adjusted (such as by the automatic circuits of the embodiments described above) until the luminescent gas or gases are just at the point of ionization (glowing). At this point, areas where there are objects below the obscuring surface (such as wall studs, electrical boxes, wiring, HVAC components, water pipes, air conditioning, heat ducts, etc.) will have a higher capacitance to earth ground, and therefore will provide a lower AC impedance to the AC voltage applied to the gas chamber and will glow, or glow more brightly, than surrounding areas. The gas in the chamber is preferably homogeneous which results in each molecule or atom of the gas, as the case may be, functioning as a detector. By this means, a highly defined, high resolution, high contrast view of the hidden objects will be provided to the user.

The use of a continuous and homogeneous gas within the chamber 522 (FIG. 5) results in a much higher resolution of detection than with the prior art use of discrete capacitive elements. Since the gas is used to form part of a capacitive sensor, it is directly responsive to the capacitance changes brought about by being placed adjacent a hidden object behind a wall, for example. The parts of the gas located adjacent a hidden object that would increase the current through the gas due to the increase in capacitance provided by that hidden object will be detected by that part of the gas. The discrete elements so often used in the prior art are not used here. Reaction of the continuous gas to capacitance changes occurs at an atomic or molecular level yielding extremely high resolution. Additionally, the method of bringing the gas just to its ionization level where the gas becomes optically visible also provides the display function of the detection device. Using the gas simultaneously both as the detecting component and the display component of the detection device in accordance with aspects of the invention results in fewer parts and reduced expense. Additionally, it effectively provides a window that shows the environment behind the obscuring surface.

Figure 11:
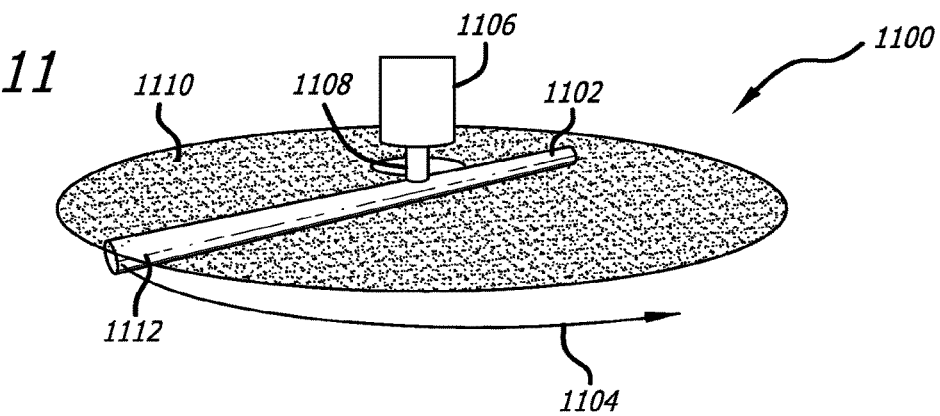
FIG. 11 is an embodiment of a capacitive detector in accordance with aspects of the invention in which a luminescent gas container is continuously rotated by a motor between a stationary electrode and an obscuring surface (not shown), the speed of rotation of the gas container is selected to be the rate of a viewer's persistence-of-vision whereby a larger and clearer image of objects detected behind an obscuring surface are displayed.

In cases where the economics of the display are critical, it would be desirable to use fewer gas-filled chambers of a possibly smaller overall volume while maintaining the ability to sense and display a large two dimensional search area. FIG. 11 discloses a detection system 1100 and method where a single gas tube may be used. In this embodiment, a single or smaller gas-filled tube or chamber may be rapidly scanned over the surface to be probed, and thus build up a line, or area, at a time of a comprehensive view of objects under an obscuring surface rather than using a large number of separate tubes as in the previous embodiment.

Here the sensing and display tube 1102 is mechanically spun in a circle 1104 by a motor 1106. The display tube 1102 is connected to the motor 1106 by a non-conductive drive shaft 1108. The tube is rotated underneath the transparent top electrode 1110 to which is applied a source of high-voltage, high frequency alternating current (not shown) as in previous embodiments. As the tube 1102 rotates and portions of it pass over objects hidden behind an obscuring surface (not shown), those portions of the tube will be illuminated as described above. If the tube rotates substantially at the human persistence-of-vision rate (the rate at which the human eye/brain blurs repetitive stimulation into a continuous image) then a continuous, two-dimensional image of objects behind the obscuring surface will be displayed.

The response of a gas to an instantaneous change in excitation is measured in $\frac{1}{1000}$ths of a second (1 millisecond range). This means that the tube 1102 can be rotated as reasonably fast as is required to exceed the persistence of vision threshold. The gas transition time to brightness is not a critical factor as it will be fast enough for any reasonable mechanical system. One only has to rotate the tube over the obscuring surface and under the energizing electrode, and the gas will instantaneously register its change from non-light-emitting, to light emitting. To get persistence of vision to work, assume that low-flicker persistence of vision occurs at 30 Hz. Then one would want to rotate the tube at 30/2=15 revolutions/second (divide by two because each end of the tube passes over the same area twice during a revolution). The RPM should be 15×60 seconds/minute =900 RPM which is achievable with many small motors. The display 1112 therefore comprises the gas filled tube 1102.

Figure 12:
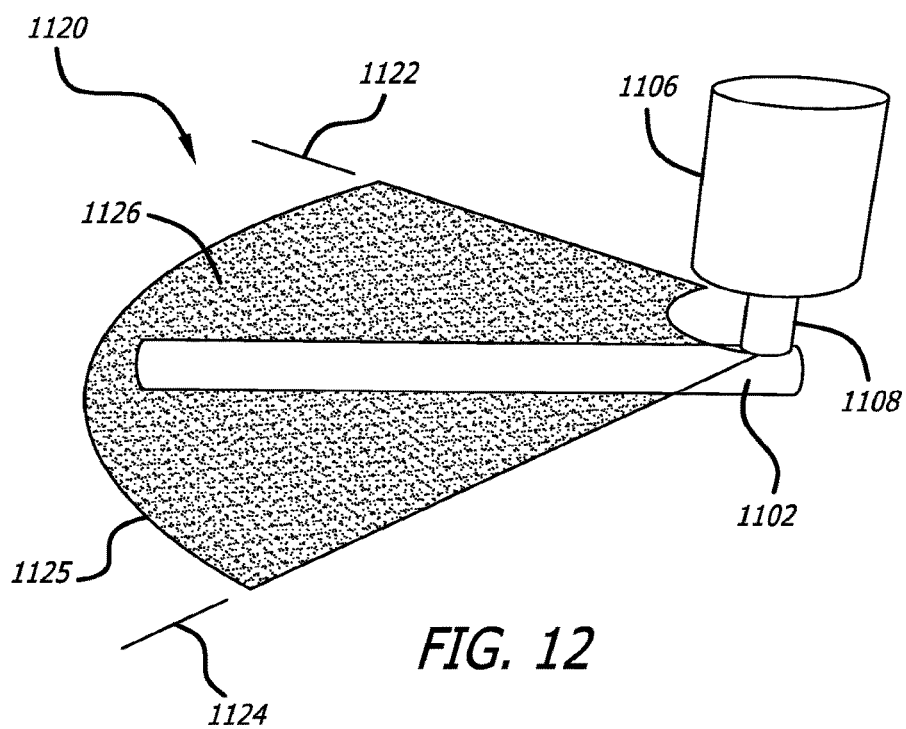
FIG. 12 is an alternate embodiment of a capacitive detection device operating similarly to the device shown in FIG. 11 except that the luminescent gas container is confined to a reciprocating rotational movement through an arc of less than a full circle with the electrode also reduced in size to cover the same sized arc. The rate of speed of reciprocation is also selected to be the rate of a viewer's persistence-of-vision.

FIG. 12 illustrates an alternate embodiment of a moving-sensor detector 1120 where the detection and display tube 1102 is not rotated through a full 360° circle by the motor 1106 and shaft 1108. Instead, the detection and display tube is reciprocally moved, or oscillated, through an arc 1125 of a circle between two extremes 1122 and 1124 on the circle. This causes a pie-shaped display 1126 and in this embodiment, the arc 1125 of the pie is less than 180°. The rate of reciprocating movement of the display tube 1102 is selected to be high enough to cause persistence-of-vision in the viewer and allow for the formation of a two-dimensional ("2D"), wedge-shaped image.

The following are three primary reasons for using the single tube:

1) To sweep out an area that would have required several tubes, thereby lowering the cost. Because the tubes may represent a substantial portion of the cost of the detector device, minimizing the number of them (even if it means trading their cost off against a motor drive) may result in a lower overall cost-to-produce;
2) To provide a two-dimensional image (which is an advantage resulting from the invention). A two-dimensional image provides a context-rich view into not just the presence of objects behind an obscuring surface, but of their shape, orientation, and interconnection; and
3) Uniformity of image. Because there can be slight differences in the "turn-on" voltage of individual tubes, there can be gray-scale variation in the image provided by multiple tubes. This can be greatly reduced by the selection of tubes with similar turn-on characteristics, but is automatically mitigated by the use of a single tube and essentially time-space multiplexing it.

In the case of FIG. 11, the motor 1106 blocks the central portion of the display 1112. Given the benefits of a large area of view (certainly larger than one could obtain with a single, or a very few, "stationary" tubes), there is still substantial advantage to using a scanning tube when cost and the presentation of a two-dimensional, context-rich, image are concerned. To mitigate the apparent view limitation, the device's case can be fashioned so that it emphasizes the arc-like or ring-like display area and where it would stylistically downplay the "blind-spot".

Figure 13:
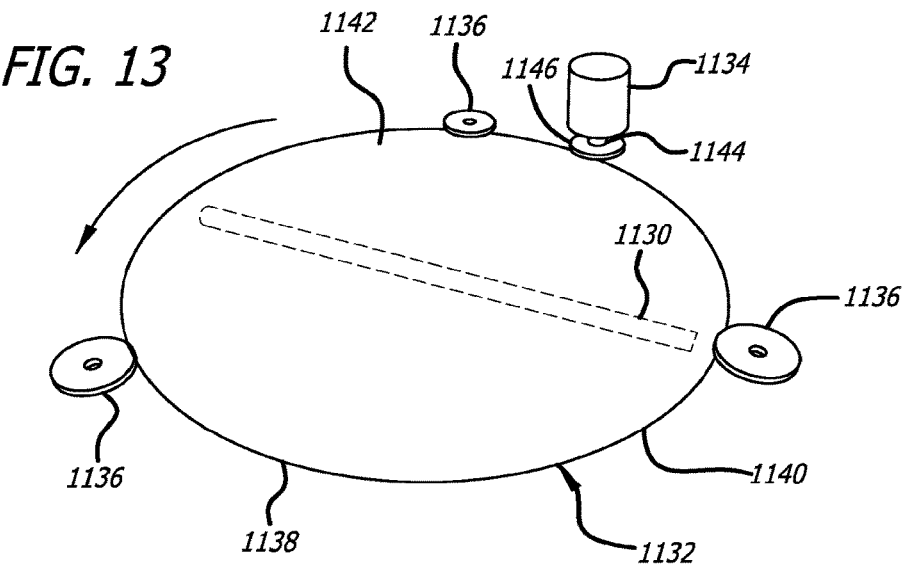
FIG. 13 shows an alternate technique of rotating a luminescent gas tube where the motor is off to the side thereby not blocking a view of any part of the gas in the tube, the motor engaging the edge of the disk in which the gas tube is mounted.

Alternatively, FIG. 13 presents an embodiment in which the center of the luminescent gas display tube is not obscured by a motor. In this embodiment, the display tube 1130 is mounted to the bottom surface 1140 of a circular disk 1132 to thereby rotate with it. The motor 1134 is coupled to the edge of the disk to apply rotational motion. Rollers 1136 support the disk at three points on its circumference 1138 in this embodiment. The disk may be described as an optically transparent backing plate, made of transparent plastic with a layer of indium tin oxide or other transparent conductor on its top surface 1142 so that it also forms the transparent electrode over the tube. Even though the top surface is optically transparent, the gas tube is shown in dashed lines to emphasize that it is attached to the bottom surface. Thus the entire disk-shaped area swept out by the rotating tube 1130 with the disk 1132 is displayed.

Figure 16:
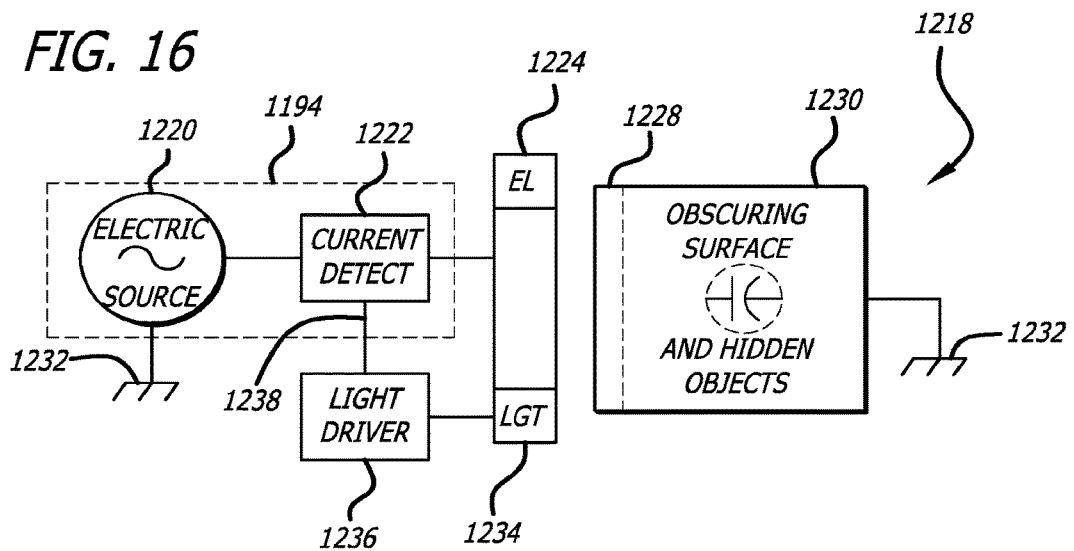
FIG. 16 is a schematic block circuit diagram of a detector circuit in which the capacitance sensed by the detector is indirectly determined by a current sensor in the line of the electrode, the current sensor output being provided to a light driver that controls the output of light from the moving electrode in accordance with the capacitance sensed, the light driver controlling the light in accordance with the persistence-of-vision of the viewer.

The transparent electrode located on the top surface 1142 of the disk 1132 can be electrically charged either by a separate electrical "brush" (not shown) that rides on the surface that carries the conductive coating or, alternatively if the conductive coating extends to a conductive edge of the rotating disk, one or more of the metal rollers 1136 that are supporting the edge of the disk can serve to bring high-voltage AC to the disk. The rollers may have a substrate of non-conductive material with a metallic coating, or may be formed in other ways. Although FIG. 13 shows the motor shaft 1144 directly driving the disk, other means may be used. For example, a belt drive may be used as shown in FIG. 16, or a friction roller, or a plastic toothed pinion gear and toothed edge on the disk. Additionally, other techniques are possible for locating an electrode above the gas tube integrated into the spinning disk.

Figure 14:
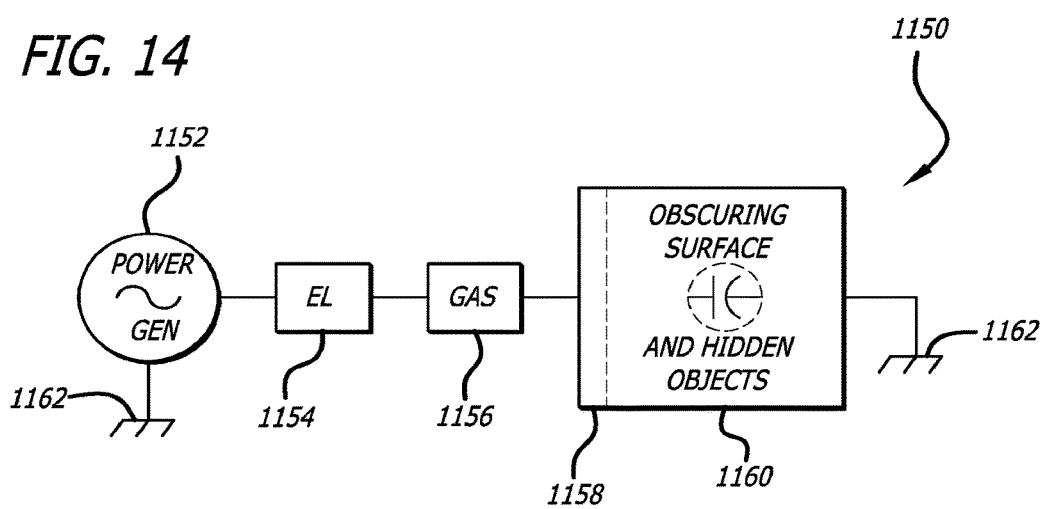
FIG. 14 is a schematic block diagram of a detector circuit in which the luminescent gas is placed in the capacitive circuit and is therefore a direct indicator of the map of hidden objects detected behind an obscuring surface.

FIG. 14 presents an overview block schematic diagram 1150 of capacitive detectors and capacitive detection methods described and shown above. An AC power generator 1152 provides AC power to an electrode 1154. The electrode conducts power to a gas 1156 that is in a container such as a tube or tubes that are placed against an obscuring surface 1158, behind which are located hidden objects 1160. Both the AC power generator 1152 and the hidden objects are in electrical contact with a common ground 1162. Thus it will be seen that the light source; i.e., the gas, is a part of the detection circuit of the hidden objects. Additionally, the AC power generator is controlled to provide power selected to cause the gas in the gas tube 1156 to provide a display when hidden objects are detected, as is discussed above. Although the diagram shows use of an earth ground 1162, other types of return paths are possible.

Figure 15:
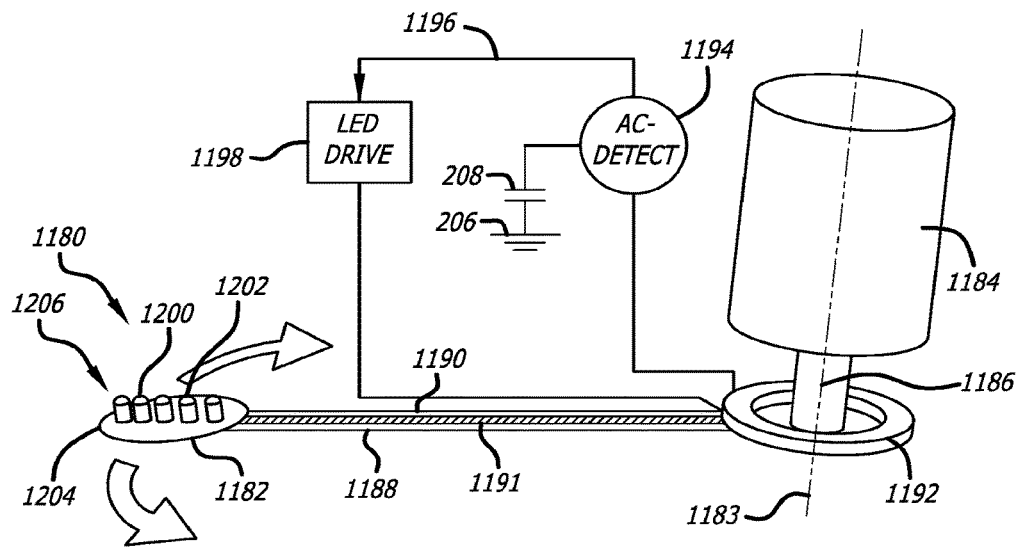
FIG. 15 is an alternate embodiment of a capacitive detection and display device in which an electrode is shown being rotated by a motor. As the electrode is rotated, the capacitance of the circuit of which it is a part is measured and a light drive controls a light source or sources mounted to the opposing side of the rotating electrode to illuminate accordingly. As in the embodiment of FIG. 11, the speed of rotation of the combination electrode/light source is a high rate selected so that the persistence-of-vision of the light source presents a larger and clearer image of objects detected behind an obscuring surface.

FIG. 15 depicts an electronic two-dimensional ("2D") hidden objects detector system 1180 and method that includes capacitance imaging of hidden objects. A detector electrode 1182 consisting of a metal pad (shown as circular in the diagram but possibly of other convenient shapes) has a predetermined pattern of movement automatically controlled by the imaging system 1180. In this embodiment, the detector electrode 1182 is rotated about a central axis 1183 in a circle by a motor 1184 via an axle 1186 and a nominally non-conductive support strut 1188. Thin electrically-conductive paths 1190 formed on the support strut connect the detector electrode through a slip ring 1192 to a capacitance detection circuit 1194. The slip ring allows continuous electrical connection to the conductors 1190 on the strut 1188 during rotation. One purpose of the conductors is to conduct detection energy to the electrode from the AC circuit 1194 to apply to an obscuring surface 104 for the purpose of detecting hidden objects 106 and 108 (see FIG. 1). The detector electrode 1182 is oriented such that as it rotates, it applies the detection energy to the obscuring surface.

The capacitance detection circuitry 1194 also monitors the capacitance between the rotating electrode 1182 and ground and reacts to an increase in detected capacitance that exceeds a threshold amount by sending a light activate signal 1196 to a light control drive 1198. Upon receiving the activate signal, the light control drive subsequently provides power to a light source 1200 that is mounted on the top side 1202 of the detector electrode which is opposite the side used by the electrode to apply energy to the obscuring surface. Thus, the light source 1200 would be visible to a user of the detection system 1180 such as, for example, if the detection system were mounted in the housing 116 shown in FIG. 1.

A significant advantage is provided by the arrangement of FIG. 15. Because the display device 1200 is co-located and integral with the electrode 1182, and the display device is controlled in accordance with the exact capacitance detected at the electrode's position, an accurate and precise display, or image, of hidden objects at the electrode's location will result.

Various ways are available to determine the capacitance sensed at the electrode's position. A current sensor is one way to do so. The current sensor senses the amount of current drawn by the electrode and from that, the amount of capacitance at the electrode's position is determined. Current sensors are well known to those skilled in the art and no further details are provided here.

In this embodiment, the display 1206 comprises five light emitting diodes ("LEDs") 1200 that are mounted to the top surface 1202 of the electrode 1182. These LEDs will provide a display 1206 of the obscuring surface and any objects hidden behind the obscuring surface. The LED power is conducted to the LEDs 1200 from the LED drive device 1198 through the slip ring 1192 and the wire conductors 1191. As the motor 1184 moves the electrode 1182 over areas of increased capacitance, the LEDs 1200 light, or light more brightly, thereby creating the display 1206. This entire structure is termed the "sensor/display pad" 1204 and in this embodiment has the electrode 1182 integrated with the display 1206. Thus a single rotating structure is provided; one that applies detecting energy to the obscuring surface (electrode 1182), one that is used to measure the capacitance at the single rotating structure (electrode 1182), and one that provides a display of hidden objects detected (1206). Although multiple conductors 1190 and 1191 are indicated by a single line on FIG. 15, they are meant to be separated as necessary to perform their respective electrical conducting functions. They are shown as a single line in FIG. 15 for convenience and to preserve clarity of the figure.

The detector electrode 1182 part of the sensor pad 1204 is electrically conductive. It may be formed of any conductive metal, or a conductive paint layered over a non-conductive substrate (and actually connected by thin conductive paint "wiring" back to the central sensing circuitry 1194) or it might take the form of a relatively conductive plastic (highly-conductive relative to air for instance).

The sensor pad 1204 is rotated at a high enough rate of speed to invoke the persistence-of-vision effect in a viewer. This will cause the lighted area to include an annular two-dimensional ("2D") ring of sensing capability. In another embodiment, more than one detector electrode can be used on the sensor pad and more than one LED or other type of visual indicator can be mounted on the sensor pad, or multiple sensor pads can be used with a sensor pad mounted adjacent another sensor pad or pads. In this manner, as the sensor pads rotate, a "rainbow" of 2-D imagery of objects hidden under an obscuring surface will be displayed.

In another embodiment, there are more than one sensor pads in, for instance, a linear array, extending out along the rotating arm (strut) 1188 from the center of rotation 1183. In this embodiment, each sensor pad is associated with a co-located (slightly to the side, or centered in the actual pad) indicator LED, or other light emitter or modulator. As the ensemble of linear elements rotates, each sensor pad capacitance-to-ground increases when over a hidden object, and instantaneously lights, or modulates the light of, its associated visual indicator. In this manner, an entire area of detection is swept at a time. Electrical conductors, such as wires, printed paths, or other electrically conductive device, connect along the rotating arm each of the individual sensor pads back to a central sensor controller which sends indicator signals back to the respective corresponding light source. Alternatively in yet another embodiment, the sensing electronics for each light source or visual indicator can be mounted on the respective sensor pad itself. In such a case, only the power for all the units then would need to be brought out along the rotating arm.

It will be noted that in the capacitive detector 1180 of FIG. 15, the light source 1200 is not a part of the circuit that detects and measures capacitance as it is in FIG. 3C, for example. In the case of FIG. 15, the light source 1200 is physically co-located with the electrode and moves with it but is not placed between the electrode and the obscuring surface. However, the light source 1200 that provides the display is directly, instantaneously, and continually controlled by the same capacitance detection circuit that includes the very electrode to which the light source is mounted.

Referring now to FIG. 16, such a hidden objects detector system using a capacitive detector circuit 1218 is shown in schematic block form. An AC electrical energy source 1220 provides energy to a capacitance detector device 1222 for measuring the amount of capacitance detected by the circuit 1218. In this embodiment, a capacitance detector 1222 is shown in series between the AC source 1220 and an electrode 1224 because a current level detector is used. However, other types of capacitance detectors may be employed. The output of the AC energy source 1220 is applied through the current detector to the electrode 1224 that is located at an obscuring surface 1228 for the purpose of detecting the existence and shapes of objects 1230 hidden behind the obscuring surface. The obscuring surface and hidden objects together create the capacitance 1230 to be detected by the capacitive detector circuit 1218. The electrical schematic sign of a capacitor is circled and included in box 1230 in FIG. 16. A ground 1232 return path exists between the signal generator 1220 and the capacitance of the obscuring surface and hidden objects 1230, although other types of return paths may be employed.

Figure 17:
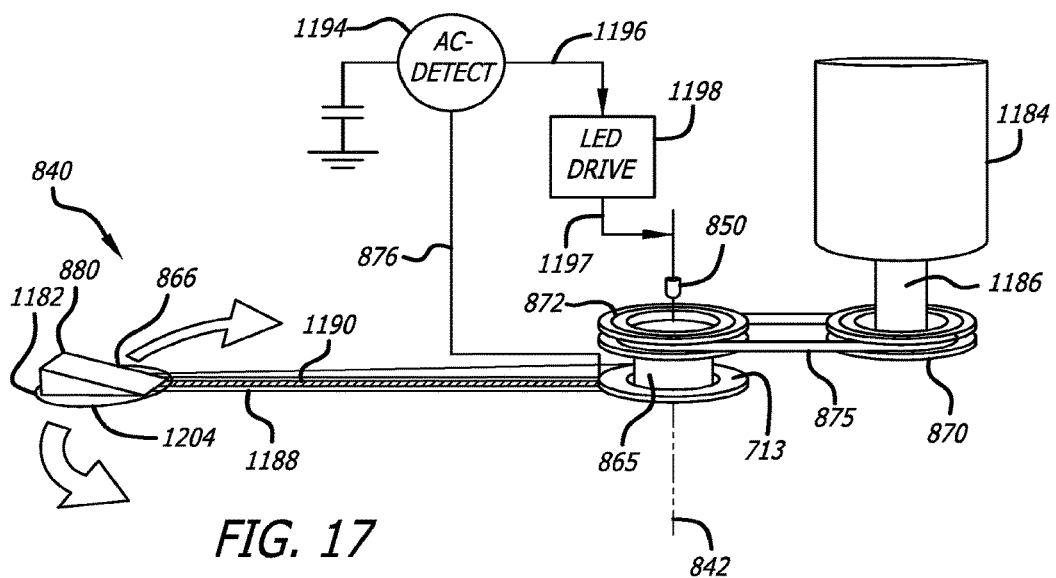
FIG. 17 is a variation of the embodiment of FIG. 7 in which the visual element comprises a rotating mirror that reflects light energy to a passive diffusing surface on the opposite side of the electrode that provides a display of varying intensity in response to a change in capacitance caused by a hidden object.

For the purposes of FIGS. 15, 16, and 17, the signal generator 1220 and current detector 1222 shown in FIG. 16 are located in the same device 1194 which is referred to generally as the AC circuit. The AC circuit may also include a controller as is shown in FIGS. 2 and 3A. In other diagrams or embodiments, these components may be separately shown and located.

In accordance with the capacitance detected by the current detector 1222, a display control signal 1238 is provided by the current detector to a light source drive 1236 which in turn, controls the illumination produced by a light source 1234 located as part of the electrode 1224. The light source may take different forms, one of which is a light emitting diode or a plurality of light emitting diodes. It will be noted that in the system of FIG. 16, the light source 1234 is not located between the electrode 1224 and the obscuring surface 1228/hidden objects 1230. This is the case in the embodiments of FIGS. 15, 16, and 17.

FIG. 17 depicts an alternative hidden objects detection and display system 840 where a detection electrode 1182 is rotated about a central axis 842 indirectly by a motor 1184 via a pulley system consisting of a motor pulley 870, a belt 875, and a hollow pulley 872. The hollow pulley 872 allows a rotational connection to a nominally non-conductive support strut 1188 while simultaneously allowing the passage of light down the support strut's hollow shaft. Conductive traces 1190 formed on the support strut connect the detection electrode 1182 through a slip ring 1192 to a capacitance detection circuit 1194.

The capacitance detection circuit in this drawing also includes a power generator (not shown) and applies the detection power from that generator to the electrode 1182 through an electrical connection wire for application to an obscuring surface and any hidden objects behind that surface. The slip ring 1192 allows continuous electrical connection to the conductive traces 1190 on the strut 1188 during rotation. The power generator and capacitance detection circuitry 1194 react to an increase in detected capacitance that exceeds a threshold by sending a light activate signal 1196 to a light source drive 1198. The light source drive will send a respective light drive signal 1197 to a light source, in this case an LED 850, to cause the light source to illuminate. Light from the illuminated LED 850 travels down the hollow pulley 872 and is reflected by a rotating 45° mirror 865 towards a passive diffusing surface 880 located at the electrode 1182. In this way, as the sensor pad 1204 moves over areas of increased capacitance, the pad 880 will be lit by, or will be lit up more brightly, by the reflected light from the rotating mirror 865. Although not shown, a controller will control the motor 1184 to rotate the strut 1188 fast enough to cause a viewer's persistence-of-vision to see a lighted area that includes an annular 2D ring of sensed hidden objects. The LED's 850 light proceeds downward through the hub (hollow pulley) 872 where it is reflected at right angles by the mirror 865 to head out towards the end 866 of the rotating arm 1188 where it illuminates the surface of an angled light diffuser 880 so that the illumination of the area at the end of the rotating arm occurs contemporaneously with the electrode 1182 passing over a high dielectric area. This is essentially "light commutation" and works because the time between capacitive detection and lighting the LED is measured in the fractional thousandths of a second.

Figure 18:
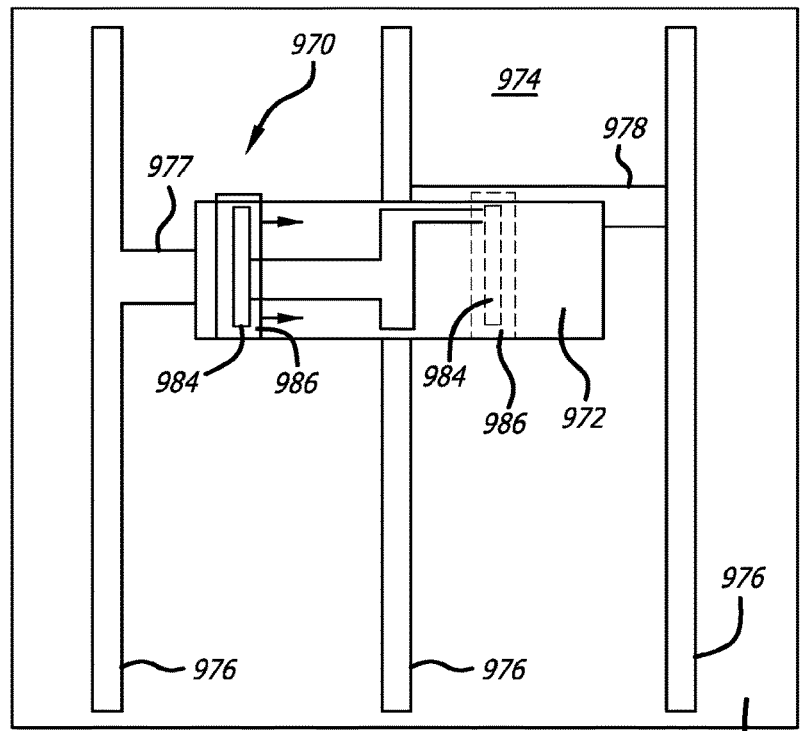
FIG. 18 is an alternate embodiment in which a sheet of phosphorescent material responsive to the wavelength of light emitted by the capacitive detection system provides a map display of the capacitive detection scan of the obscuring surface. In this case, a movable single tube sandwiching the phosphorescent sheet between it and the obscuring surface is shown with the phosphorescent sheet being much larger than the gas container. The phosphorescent sheet is responsive to the frequency of light from the gas tube and the chemical formulation of the phosphorescent sheet is selected so that the sheet has an image persistence that continues for a period of time allowing a map to be made of the items behind the obscuring surface.

In one embodiment, the electrode has an overall area that is significantly larger than the electrical paths going out to it so that substantially all of the capacitive current being detected is due to the electrode. If there is only a single LED or a small group acting as a single indicator, then this device only plots out a "circle of display." If the entire system is duplicated (only one ultimate AC source would be needed), with several corresponding AC current detectors each driving a separate LED driver, and the LEDs are arranged radially along the shaft approximately coincident with the electrodes, then an array of concentric circles of detection would be swept out FIG. 18 illustrates an embodiment of a hidden object detection device 970 where measurements of capacitance are memorialized through the use of a phosphorescent sheet 972 of material layered over the general area 974 where it is desired to view objects behind an obscuring surface. An exemplar arrangement of studs 976 and cross braces 977 and 978 are shown behind an obscuring surface 980, although the obscuring surface is not clearly shown and the studs and cross braces are depicted in solid lines as opposed to dashed lines for clarity of illustration.

In this case, a phosphorescent sheet 972 has been attached to a position on the obscuring surface, such as a wall 980, and is held in place on the wall by common means. As examples, the phosphorescent sheet is held against the wall by tape, by tacks, or by a user simply holding it in position by hand. The electrode 986 is visually transparent, the gas tube 984 located between the electrode and the obscuring surface produces an illuminated display through use of a luminescent gas, and the phosphorescent sheet 972 holds that display produced by the gas tube as the gas tube is moved across the sheet. The significant effect that the phosphorescent sheet has on the embodiment is shown in FIG. 18 where the gas tube and associated electrode have been moved across the obscuring surface 980 covered by the phosphorescent sheet from the position at the left of the figure in which it is shown in solid lines to the position at the right of the figure at which it is shown in dashed lines. The phosphorescent sheet has held the display created by the gas tube as it was moved from left to right. Portions of two cross braces 977 and 978 can be seen on the phosphorescent sheet 972 as well as a portion of a vertical stud 976.

A hidden object detector device such as one disclosed herein as FIG. 2 that includes a luminescent gas can be used in the embodiment of FIG. 18. Other embodiments of light emitters used to provide a visual display will also function well. The tube and electrode are placed on top of the phosphorescent sheet 980 and the electrode is powered in accordance with principles disclosed above. The luminescent gas in the tube 984 will then illuminate in accordance with the capacitance detected and thus create an image of hidden objects, in this case a stud 976 and two cross braces 977 and 978. The phosphorescent sheet will hold that image for a length of time depending on its chemical composition.

Those areas where the illumination device 984 glows will cause the phosphorescent material to light up, and stay lit, for a period of time adjustable by the chemical formulation of the phosphorescent sheet, but in any event from several seconds to several minutes. During this time, the phosphorescent sheet becomes a map 960 of the objects under the surface. This technique allows large areas to be mapped with a small detector of the gas filled or electronic type. It also allows for cutting holes in walls very accurately, based on the lingering map of the phosphorescent sheet, and its use as a low-cost sacrificial template for a cutting, drilling, or the nailing/screwing process.

A handheld luminescent gas tube 984 can be manually scanned over the phosphorescent sheet 972. The direction of scan is not important, and a user can "rub" back and forth over an area that he or she wants to "burn in" (expose to more exciting light). Alternatively, a motorized rotating, or translating (as on a belt), set of sensor pads with UV LEDS facing downwards to expose the phosphorescent sheet while visible light LEDs face upwards (to give the user immediate feedback on the detection), may be employed. If the sheet is fluorescent (which means "only lights, or lights with very short persistence, when external excitation exists"), then one would have to provide enough persistence in the fluorescent material so that the image remains visibly bright with low flicker while the device is against the surface. Long-persistence phosphorescent sheets may be used and these continue to glow, even after excitation has been removed. If the illuminating gas tube/detector is moved over such a material, the dark areas (where there is no high-capacitance object below the surface) will always stay dark, no matter how long the tube is placed against that area of the surface. Similarly the areas with a high-capacitance object behind them will light areas of a tube and charge up the phosphorescent sheet in that area, and when the charging tube is taken away, the glowing image of the high-capacitance areas will remain (possibly for several minutes for a long persistence phosphor).

In another embodiment, the hidden object image illuminations devices shown herein can leave a semi-permanent image of an area under an obscuring surface by laying a sheet of material that glows in a semi-sustained manner when exposed to light, over that surface. This becomes especially efficacious if the gas used as the detection media glows at a wavelength that best induces phosphorescence in the sheet material.

An advantage of these solid state systems is that less than 20 volts of alternating current ("AC") is required to be able to detect a change in AC current through the obscuring surface (given that amplified current detectors can be used). However the obvious disadvantage is that the resolution of the device is now determined by the number of electrodes which of course are finite in number and of significant size (thus lower resolution).

Although described above for use with a few applications, it should be noted that a hidden object detection device in accordance with the invention may be usable with numerous applications. As examples of some other uses, such a detector would be useful in determining construction issues in airplanes/boats with non-conductive hulls. Such a detector may also be useful in locating explosives that are hidden in walls or behind other obscuring surfaces. It can also be used to determine whether a person is wearing a false leg or other body part. A person hiding on the other side of a wall surface, someone behind a door, or someone hiding inside a boat or other vessel can also be "seen."

Further applications include analyzing composite sheet materials to locate thickness or seam inconsistencies, analyzing fiberglass boat hulls to locate seams, locating materials underwater (different density of water vs. other materials), locating contraband on a person, locating where things are not (e.g. determining that something is solid), determining where "blind" holes in large fiberglass structures need to be (e.g. a person gets inside a large plastic pipe, and can find areas outside the pipe that are locations where fasteners need to go through).

Yet other applications include determining the fit of shoes since human tissue will show up against the less "wet" (conductive), leather or rubber, finding high frequency electric fields (tuning the phase of the electrostatic exciting field for the gas), detecting in a wiring harness a particular wire and whether it is broken, determining when something metallic is more, or less, connected to ground, locating anything conductive that has a reasonable capacitance to ground, finding conductive particles in non-conductive backgrounds, detecting the shape of the residue of a conductive liquid as it evaporates (for instance a solution of lightly salted water leaving behind a conductive layer of brine).

Additional applications include detecting and tracking a guide wire behind a wall/floor surface (to steer a vehicle autonomously), determining in medical applications where someone is on a non-metallic gurney from underneath without requiring invasive radiation, seeing how well a cast fits a patient. Further applications include detecting whether, and where, water is in a plastic pipe, detecting the flow of water or other liquids in plastic, or other non-conductive pipes, detecting the exact "shape" of water in a container from the bottom, for instance, being able to detect water in a shallow plastic "pan," being able to see the flow of a conductive gas, or a conductive liquid dissolved in a non-conductive fluid, or to discern liquids with different dielectric constants, looking through fabrics during manufacture to see indexing "marks" (possible to make these marks, or hidden images, of flexible conductors), looking through large sheets of plywood to determine when they are lining up with machines that are about to cut or shape them in other ways, detecting a path on a printed circuit board and when that path is broken, finding the low spot in a container by looking at the pattern of water collecting in the (nominally) flat-bottom container, looking to see whether plated-on conductive coatings on plastics are effective, finding conductive ores in non-conductive slurries.

Further applications include looking through clothing to see what the fit is on someone wearing it (what part of the area underneath the clothing is "air" and what part is "flesh"), detecting a metallic pattern that can be painted onto a surface; "find the hidden message," detecting hidden patterns in thread in fabrics (could be used for sending secret messages), or as a novelty device to see hidden messages in fabrics, displaying a pattern made up of simple wire behind a fabric, detecting hidden messages for games, real-time painting with conductive ink, and being able to see the image that you painted in neon light, painting in conductive ink (or perhaps somewhat conductive water, or just water), and doing it over one of the detectors configured in accordance with the present invention, such that the UV that is emitted causes phosphor to glow, thus giving real time painting on phosphors with just water. And finally, the invention is usable to provide a system that allows a device to self-level when it looks at the pattern of a conductive liquid in a vessel.

Voltages would typically be alternating current at approximately 6 KV (6,000) volts peak-to-peak, and at frequencies of from typically 30 to 60 kHz. It should be pointed out that this high voltage is delivered at extremely low currents and as a result, does not present a safety hazard to human users. Additionally the device enclosure can be made completely non-conductive and sealed, eliminating direct human contact with the high voltage supply, and interlocks can be used (switches that open to prevent current flow) if the unit should be opened, for instance, to change its batteries.

Typically the noble gasses: neon, krypton, argon, etc., would be used as they emit highly visible light. However as is common practice in the manufacture of fluorescent tubes, the gas used may emit, light of an invisible wavelength (for instance ultraviolet), in this case, the insides of a tube are lined with a phosphor that responds to the UV-emitted by the gas and converts that invisible light to visible light.

Although described and shown in terms of using a luminescent gas, other materials having visual display characteristics that vary in response to electrical energy or fields or other energy impressed upon them may be used. Liquid crystal material, electro-chromic devices sometimes known as "smart glass," and other materials may be usable. These materials may produce their own light, such as luminescent materials, or may be assisted by the provision of other light sources. They may be front lit or backlit, depending on the particular application for the invention.

Both types of tube are usable, however, gases with the lowest "breakover" voltage (voltage at which the gas ionizes, and begins to emit light) are preferred.

The terms "tube" and "chamber" are often used interchangeably herein to mean the same thing.

When LEDs are used, the actual LED indicators only require a few volts, typically 1.5 to 3.5 volts to light; however, they are driven by detection circuits that may require several tens of volts of AC excitation delivered to the sense electrode(s) so that the voltage divider presented by the in-wall capacitance still provides enough of a signal to the detector for it to function properly.

The embodiments described and shown herein are to be considered in all respects as illustrative and not restrictive. Although the present invention has been described in terms of certain preferred embodiments, other embodiments that are apparent to those of ordinary skill in the art are also within the scope of the invention. Accordingly, the scope of the invention is intended to be defined only by reference to the appended claims.

I claim:

1. A device for detecting and displaying an object hidden behind an obscuring surface, the hidden object having a dielectric constant, the detecting and displaying device comprising:
   an energy source;
   a detecting electrode connected to the energy source and producing an electric field therefrom;
   a chamber located between the detecting electrode and the obscuring surface within the electric field produced by the detecting electrode, the chamber comprising;
   a visual display material, the visual display material having a visual display characteristic that is varied in response to the strength of the electric field applied to it by the detecting electrode and in response to the dielectric constant of the hidden object;

a display area through which the visual display characteristic of the visual display material can be seen; and a sensitivity enhancement device located between the chamber and the obscuring surface within the electric field produced by the detecting electrode, the sensitivity enhancement device comprising a sensitivity electrode that directs and intensifies the electric field produced by the detecting electrode towards the obscuring surface and hidden object so that the detecting and displaying device has increased sensitivity and penetrating depth through the obscuring surface to result in detecting and displaying the hidden object;

wherein a change in capacitance caused by the hidden object is detected by the visual display material and the shape of the hidden object is displayed in the display area of the chamber by the varying of the visual display characteristic of the display material;

whereby the visual display material is used to both detect and display the hidden object.

2. The device for detecting and displaying of claim 1 wherein the sensitivity electrode comprises a printed line electrical conductor on a non-electrically conductive substrate.

3. The device for detecting and displaying of claim 1 wherein the sensitivity enhancement device comprises a pattern of sensitivity electrodes located between the chamber and the obscuring surface within the electric field produced by the detecting electrode, each of the sensitivity electrodes acting to increase the sensitivity of the detecting and displaying device.

4. The device for detecting and displaying of claim 3 wherein the pattern comprises an array of electrical conductors in the shape of at least one of lines, dots, and circles.

5. The device for detecting and displaying of claim 3 wherein the pattern comprises an array of printed line electrical conductors on a non-electrically conductive substrate.

6. The device for detecting and displaying of claim 5 wherein the substrate is formed of at least one of clear, translucent, reflective, and opaque material on which electrical conductors are placed.

7. The device for detecting and displaying of claim 1 wherein the visual display material emits light; and further comprising a substrate on which the sensitivity enhancement device is mounted between the chamber and the obscuring surface wherein the substrate is colored to enhance at least one of contrast and brightness of the light emitted by the visual display material.

8. The device for detecting and displaying of claim 1 wherein the chamber comprises a serpentine tube containing a luminescent visual display material.

9. The device for detecting and displaying of claim 1 wherein the chamber comprises a plurality of separate tubes located adjacent each other, each of which contains a luminescent visual display material.

10. The device for detecting and displaying of claim 9 wherein each of the plurality of separate tubes comprises a cold cathode fluorescent lamp.

11. The device for detecting and displaying of claim 9 further comprising micro-louver material located over the plurality of tubes configured to pass light in a particular direction.

12. The device for detecting and displaying of claim 1 further comprising a transparent optical filter applied over the display area, the optical filter configured to selectively pass light of a color generated by the visual display material and to reject ambient light thereby increasing the contrast of the displayed image.

13. The device for detecting and displaying of claim 1 further comprising a phosphorescent sheet located between the chamber and the obscuring surface;

wherein the visual display material emits light that is varied in response to the strength of the electric field applied to it by the detecting electrode and in response to the dielectric constant of the hidden object thereby creating an illuminated display of an image of the hidden object that is directed toward the phosphorescent sheet which is configured to hold the display for a length of time dependent on its chemical composition.

14. A device for detecting and displaying an object hidden behind an obscuring surface, the hidden object having a dielectric constant, the detecting and displaying device comprising:

an energy source;

a detecting electrode connected to the energy source and producing an electric field therefrom;

an array of separate tubes located adjacent each other, wherein each of the tubes contains a visual display material that emits light when activated, the array of a plurality of tubes being located between the detecting electrode and the obscuring surface within the electric field produced by the detecting electrode wherein the light emitted by the visual display material of each of the tubes is varied in response to the strength of the electric field applied to it by the detecting electrode, and in response to the dielectric constant of the hidden object;

wherein the array of tubes further comprises a display area through which the colored light emitted by the visual display material of the tubes can be seen; and a sensitivity enhancement device located between the array of tubes and the obscuring surface within the electric field produced by the detecting electrode, the sensitivity enhancement device comprising an array of sensitivity electrodes that direct and intensify the electric field produced by the detecting electrode so that the detecting and displaying device has increased sensitivity and penetrating depth through the obscuring surface to detect and display the hidden object;

wherein a change in capacitance caused by the hidden object is detected by the visual display material and the shape of the hidden object is displayed by light emitted by the visual display material of the array of tubes;

whereby the visual display material is used to both detect, and emit light to display, the hidden object.

15. The device for detecting and displaying of claim 14 wherein the array of sensitivity electrodes comprises an array of printed line electrical conductors on a non-electrically conductive substrate, wherein the substrate is formed of at least one of clear, translucent, reflective, and opaque material on which electrical conductors are placed.

16. The device for detecting and displaying of claim 15 wherein the substrate is colored to enhance at least one of contrast and brightness of the light produced by the visual display material.

17. The device for detecting and displaying of claim 16 further comprising a transparent optical filter applied over the display area, the optical filter configured to selectively pass light of a color generated by the visual display material, and to reject ambient light thereby increasing the contrast of the displayed image.

18. A method of detecting and displaying an object hidden behind an obscuring surface, the hidden object having a dielectric constant, the detecting and displaying method comprising:

producing an electric field by a detection electrode connected with an energy source;

applying the electric field to a chamber located between the electrode and the obscuring surface to activate a visual display material located in the chamber, the visual display material having a visual display characteristic that is varied in response to the strength of the electric field applied to it by the electrode and in response to the dielectric constant of the hidden object;

displaying the activated visual display material in a display area of the chamber; and enhancing the sensitivity of the chamber to the hidden object that is hidden by the obscuring surface by locating a sensitivity electrode between the chamber and the obscuring surface, the sensitivity electrode being configured to direct and intensify the electric field produced by the detecting electrode so that the increased sensitivity and penetrating depth of the chamber through the obscuring surface results in detecting and displaying a hidden object;

wherein a change in capacitance caused by the hidden object is detected by the visual display material and the shape of the hidden object is displayed in the display area of the chamber by the varying of the visual display characteristic of the display material;

whereby the visual display material is used to both detect and display the hidden object.

19. The method of detecting and displaying an object of claim 18 wherein the step of enhancing the sensitivity of the chamber comprises locating an array of electrodes between the chamber and the obscuring surface.

20. The method of detecting and displaying an object of claim 18 wherein the step of applying the electric field to a chamber comprises applying the electric field to a plurality of separate tubes located adjacent each other, each tube of which contains a visual display material.

* * * * *